(12) United States Patent
Shetty

(10) Patent No.: US 10,653,741 B2
(45) Date of Patent: May 19, 2020

(54) HERBO-MINERAL FORMULATION FOR THE TREATMENT OF CARDIO VASCULAR DISEASES AND METHOD OF PREPARATION THEREOF

(71) Applicant: Muniyal Ayurvedic Research Centre, Manipal (IN)

(72) Inventor: M Vijayabhanu Shetty, Manipal (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 0 days.

(21) Appl. No.: 16/231,858

(22) Filed: Dec. 24, 2018

(65) Prior Publication Data

US 2019/0117717 A1     Apr. 25, 2019

Related U.S. Application Data

(63) Continuation of application No. 15/960,327, filed on Apr. 23, 2018, now abandoned.

(60) Provisional application No. 62/490,213, filed on Apr. 26, 2017.

(51) Int. Cl.
| | |
|---|---|
| *A61K 36/00* | (2006.01) |
| *A61K 36/59* | (2006.01) |
| *A61K 45/06* | (2006.01) |
| *A61K 9/14* | (2006.01) |
| *A61K 36/8965* | (2006.01) |
| *A61K 36/899* | (2006.01) |
| *A61K 9/20* | (2006.01) |
| *A61K 36/185* | (2006.01) |
| *A61K 36/324* | (2006.01) |
| *A61K 36/47* | (2006.01) |
| *A61K 36/81* | (2006.01) |
| *A61K 33/00* | (2006.01) |

(52) U.S. Cl.
CPC ............. *A61K 36/59* (2013.01); *A61K 9/148* (2013.01); *A61K 9/205* (2013.01); *A61K 33/00* (2013.01); *A61K 36/185* (2013.01); *A61K 36/324* (2013.01); *A61K 36/47* (2013.01); *A61K 36/81* (2013.01); *A61K 36/899* (2013.01); *A61K 36/8965* (2013.01); *A61K 45/06* (2013.01)

(58) Field of Classification Search
None
See application file for complete search history.

(56) References Cited

PUBLICATIONS

The Government of India, Biological Diversity Act, 2002.†

† cited by third party

*Primary Examiner* — Qiuwen Mi
(74) *Attorney, Agent, or Firm* — Pilloff Passino & Cosenza LLP; Sean A. Passino; Rachel K. Pilloff

(57) ABSTRACT

Herbo-mineral formulation for the treatment of Cardio vascular diseases and method of preparing the same are disclosed herein. The disclosed herbo-mineral formulation includes herb and mineral components which facilitate in treating Cardio vascular diseases. Cardio vascular diseases may include any condition associated with heart and blood vessels. Further, the disclosed formulation may also be instrumental as anti-oxidating, anti-stress, hypolipidemic, atherogenic, antihypertensive, apoptotsis inhibiting and cardio-protective agent.

14 Claims, 12 Drawing Sheets
Specification includes a Sequence Listing.

Values were expressed in Mean±SEM (n=6);
, ## - denotes P<0.05 and 0.01 respectively (Comparison between Normal and Positive control);
*, ** - denotes P<0.05 and 0.01 respectively (Comparison between Positive control and other treatment groups).

Values were expressed in Mean±SEM (n=6);
, ## - denotes P<0.05 and 0.01 respectively (Comparison between Normal and Positive control);
*, ** - denotes P<0.05 and 0.01 respectively (Comparison between Positive control and other treatment groups Values were expressed in Mean±SEM (n=6); #, ## - denotes P<0.05 and 0.01 respectively (Comparison between Normal and Positive control);
*, ** - denotes P<0.05 and 0.01 respectively (Comparison between Positive control and other treatment groups).

Values were expressed in Mean±SEM (n=6); #, ## - denotes P<0.05 and 0.01 respectively (Comparison between Normal and Positive control);
*, ** - denotes P<0.05 and 0.01 respectively (Comparison between Positive control and other treatment groups)

US 10,653,741 B2

SEQUENCE LISTING

```
<160> NUMBER OF SEQ ID NOS: 8

<210> SEQ ID NO 1
<211> LENGTH: 19
<212> TYPE: DNA
<213> ORGANISM: Rattus norvegicus
<220> FEATURE:
<221> NAME/KEY: primer_bind
<222> LOCATION: (1)..(19)

<400> SEQUENCE: 1
gagtgtctcc ggcgaattg                                                  19

<210> SEQ ID NO 2
<211> LENGTH: 19
<212> TYPE: DNA
<213> ORGANISM: Rattus norvegicus

<400> SEQUENCE: 2
tggtgagcga ggcggtgac                                                  19

<210> SEQ ID NO 3
<211> LENGTH: 19
<212> TYPE: DNA
<213> ORGANISM: Rattus norvegicus

<400> SEQUENCE: 3
cgggagatcg tgatgaagt                                                  19

<210> SEQ ID NO 4
<211> LENGTH: 19
<212> TYPE: DNA
<213> ORGANISM: Rattus norvegicus

<400> SEQUENCE: 4
ccaccgaact caaagaagg                                                  19

<210> SEQ ID NO 5
<211> LENGTH: 18
<212> TYPE: DNA
<213> ORGANISM: Rattus norvegicus

<400> SEQUENCE: 5
ctggactgcg gtattgag                                                   18
```

```
<210> SEQ ID NO 6
<211> LENGTH: 17
<212> TYPE: DNA
<213> ORGANISM: Rattus norvegicus

<400> SEQUENCE: 6
gggtgcggta gagtaag                                                17

<210> SEQ ID NO 7
<211> LENGTH: 22
<212> TYPE: DNA
<213> ORGANISM: Rattus norvegicus

<400> SEQUENCE: 7
ggatgcccgt gctgccgagg ag                                          22

<210> SEQ ID NO 8
<211> LENGTH: 21
<212> TYPE: DNA
<213> ORGANISM: Rattus norvegicus

<400> SEQUENCE: 8
agtgaaggga ctagcattgt c                                           21
```

HERBO-MINERAL FORMULATION FOR THE TREATMENT OF CARDIO VASCULAR DISEASES AND METHOD OF PREPARATION THEREOF

CROSS REFERENCE TO RELATED APPLICATION

This application is a continuation of the U.S. application Ser. No. 15/960,327, filed Apr. 23, 2018, which in turn claims priority of the U.S. provisional application 62/490,213 filed on Apr. 26, 2017, the contents of which are incorporated herein by reference

TECHNICAL FIELD

The embodiments disclosed in this specification relates to herbo-mineral formulation effective in treatment and prevention of Cardio vascular and related complications. It also relates to the process of preparation of such formulation.

BACKGROUND

Cardiovascular diseases (CVDs) have been observed to be one of the leading causes of death globally. It is a group of diseases that are associated with heart and blood vessels. It includes diseases such as Coronary artery disease, Cardiovascular disease, hypertensive heart disease, peripheral arterial disease, etc.

Atherosclerosis, a condition wherein plaque builds-up in the arteries, is a leading cause of CVD. The risk factors of CVD include high blood pressure, hypertension, stress, hyperlipidemia, Diabetes, physical inactivity, Obesity, etc. These are the risk factors that may be regulated to prevent CVDs. There also exists other risk factors such as old age, gender, family history, etc. that cannot be regulated.

Most CVDs can be prevented by mitigating the established risk factors. Implementation of certain lifestyle modifications such as maintaining a healthy diet, limited alcohol consumption, tobacco cessation, reduced sugar consumption, stress management, etc alone can prove helpful in mitigating the risk of developing CVDs. However, if lifestyle modifications prove to be inadequate in preventing CVD, medication or medical procedure may be necessary.

Being one of the leading causes of death globally, extensive research in order to develop drugs capable of treating CVD has been performed. Modern medicine offers a wide array of drugs for the same. Treatments with these medicines depend on the type of CVD. The various types of drugs include ACE inhibitors, Antiarrhythmic, Angiotensin II receptor blockers, Calcium Channel blockers, Digoxin, Diuretics, Nitrates, etc. However, managing CVDs may be a lifelong effort and may require extensive usage of medication. Allopathic interventions often have an untoward or undesirable side effect when used extensively.

Alternatively, ayurvedic interventions have also been known in treating Cardiovascular Diseases. Many herbal formulations have been developed based on the knowledge of the healing properties of various herbs. However, the effectiveness of such formulations is arguable. There exists a need for an effective method of treating/managing Cardiovascular Diseases.

OBJECTS OF THE DISCLOSED EMBODIMENTS

The principal object of the embodiments disclosed herein is to provide a composition and method for treating Cardio vascular diseases.

A second object of the embodiments disclosed herein is to provide a composition and method for preventing Cardio vascular diseases.

Another object of the embodiments disclosed herein is to provide a herbo-mineral formulation and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which.

DETAILED DESCRIPTION

Figure 1A:
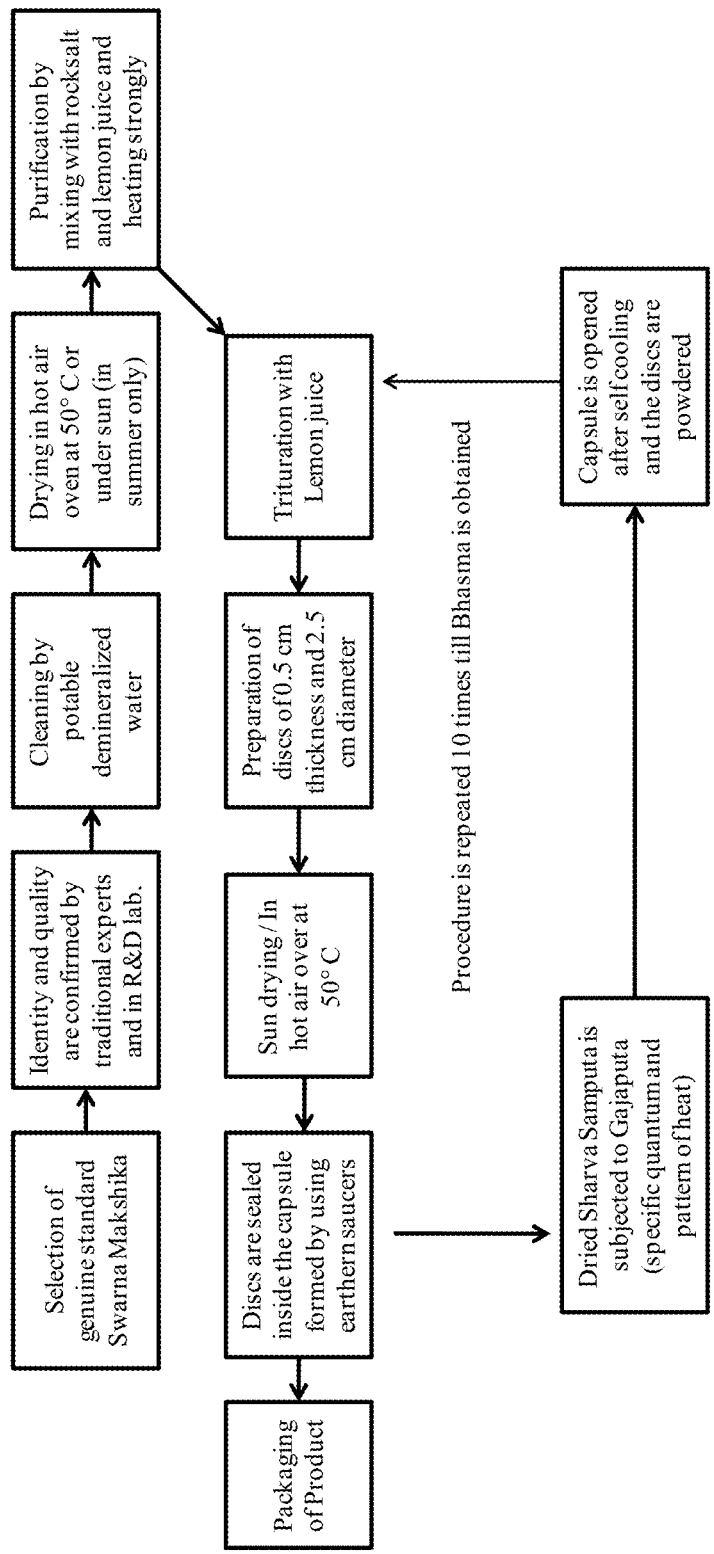
FIG. 1(a) depicts a flowchart for the preparation of Swarna Makshika Bhasma.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a herbo-mineral formulation of therapeutic value, and a process for the preparation of the formulation. The herbo-mineral formulation disclosed herein is useful in the treatment and prevention of Cardiovascular diseases and complications related to cardiovascular system. In the various embodiments herein, cardiovascular Diseases may include any condition associated to heart and blood vessels such as cardiac arrhythmias, ischemic heart diseases, coronary artery disease, valve defects, etc. Further, the complications related to cardiovascular system may be any condition generally known to be related to or considered as risk factors of CVDs including hypertension, increased blood sugar, hyperlipidemia, etc. The disclosed formulation also find use as an anti-oxidating, anti-stress, hypolipidemic, atherogenic, antihypertensive, apoptotsis inhibiting and cardio-protective agent. Accordingly, the embodiments disclosed herein achieve a method for the treatment/prevention of Cardiovascular diseases. Also disclosed are embodiments of a method of reducing the risks of Cardiovascular diseases.

Formulation

The disclosed embodiments herein provide herbo-mineral formulation having herbs and minerals. In an embodiment, the herbo-mineral formulation includes a herb component and a mineral component. In another embodiment, the herbo-mineral formulation includes a herb component, a mineral component and a suitable excipient.

Herb Component

In an embodiment, the herb component includes the herbs *Terminalia arjuna, Sida rombifolia, Withania somnifera, Tinospora cordifolia, Punica granatum, Embelia ribes, Rubia cordifolia, Nardostachys jatamansi, Emblica officinalis, Terminalia chebula, Terminalia bellerica, Piper longum, Piper nigrum, Zingiber officinalis, Boerhavia diffusa, Bamboo manna, Madhuka indica, Azhadirachta indica, Picrorhiza kurroa, Holy basil, Commiphora mukul, Steriospermum suaveolens, Premna mucronata, Gmelina arborea, Aegle marmelos, Oroxylum indicum, Desmodium gangeticum, Uraria picta, Solanum indicum* and *Solanum xanthocarpum* or their extracts, or the active ingredients extracted from these herbs.

In an embodiment, the herb component may include the herb as a whole or may include specific parts of the herb such as roots, fruits, stem, leaves, rhizome, etc. In an embodiment, the herb component includes stem bark of *Terminalia arjuna*; root of *Sida rombifolia, Withania somnifera, Rubia cordifolia, Nardostachys jatamansi, Boerhavia diffusa, Picrorhiza kurroa, Steriospermum suaveolens, Premna mucronata, Gmelina arborea, Aegle marmelos, Oroxylum indicum, Solanum indicum*; fruit of *Embelia ribes, Emblica officinalis, Terminalia chebula, Terminalia bellerica, Piper longum, Piper nigrum, Tribulus terrestris*; bark of *Azhadirachta indica*; plant of *Solanum xanthocarpum, Uraria picta, Desmodium gangeticum*; stem of *Tinospora cordifolia*; fruit pericarp of *Punica granatum*; rhizome of *Zingiber officinalis*; exudate of *Bamboo manna*; flower of *Madhuka indica*; leaves of *Holy basil* and gum resin of *Commiphora mukul* or their extract. However, it is also within the scope of the claims for the herb component to include other parts of the herb such as leaf, flowers, etc. without otherwise deterring intended function of the herbo-mineral formulation.

Herbs (in whole or part), disclosed herein, maybe included in the formulation in any form that is generally known in the field. For example, the herbs may be processed to form extracts, dried, powdered, pelleted, concentrated, etc. In an embodiment, the herbs are dried and powdered which is further incorporated into the formulation.

In an embodiment, the herb component includes *Terminalia arjuna* in an amount in the range of 8 to 12 wt %, *Sida rombifolia* in an amount in the range of 2 to 6 wt %, *Withania somnifera* in an amount in the range of 2 to 6 wt %, *Tinospora cordifolia* in an amount in the range of 2 to 6 wt %, *Punica granatum* in an amount in the range of 2 to 6 wt %, *Emblica officinalis* in an amount in the range of 2 to 6 wt % and *Commiphora mukul* in an amount in the range of 2 to 6 wt %. Further, in another embodiment, the herb component includes at least one of *Embelia ribes, Rubia cordifolia, Nardostachys jatamansi, Terminalia chebula, Terminalia bellerica, Piper longum, Piper nigrum, Zingiber officinalis, Boerhavia diffusa, Bamboo manna, Madhuka indica, Azhadirachta indica, Picrorhiza kurroa, Holy basil, Steriospermum suaveolens, Premna mucronata, Gmelina arborea, Aegle marmelos, Oroxylum indicum, Desmodium gangeticum, Uraria picta, Solanum indicum, Solanum xanthocarpum* and *Tribulus terrestris*, preferably in an amount of ≤4 wt %.

Mineral Component

In an embodiment, the mineral component includes Bhasmas or calcined preparations such as Swarna Makshika bhasma, Abhraka bhasma, Loha bhasma, Muktasukti bhasma, and Pravala bhasma. Alternatively, the mineral component may also be selected from a group consisting of at least one of Iron, Mica, Copper pyrite and Coral. In the disclosed embodiments, the bhasmas along with the herb component form bioavailable herbo-mineral complexes which are useful in treating Cardio vascular Diseases and related complications. In another embodiment, the mineral component further includes Shilajit. However, it is also within the scope of claims provided herewith for the herbo-mineral formulation to include, as a substitute or additionally, other similar calcined preparations or minerals without otherwise deterring from the intended function of the herbo-mineral formulation.

In an embodiment, the mineral component includes shilajit in the range of 1 to 4 wt %. In another embodiment, the mineral component includes Muktasukti bhasma in an amount of ≤2 wt %, Loha bhasma in an amount of ≤2 wt %, Abhraka bhasma in an amount of ≤3 wt %, Swarnamaksika bhasma in an amount of ≤2 wt % and Pravala bhasma in an amount of ≤2 wt %.

The disclosed formulation, in the various embodiments herein, may further include a suitable excipient. The list of suitable excipients includes solvents, binders, lubricants, herbal carriers, oils and salts that are generally known in the art. In an embodiment, the excipient includes acacia gum.

Further, the amount of herb component and mineral component that may be included in the various embodiments of the disclosed formulation may be in the range of 0 to 12 wt %. In an embodiment, the formulation includes *Terminalia arjuna* (8 to 12 wt %), *Sida rombifolia* (2 to 6 wt %), *Withania somnifera* (2 to 6 wt %), *Tinospora cordifolia* (2 to 6 wt %), *Punica granatum* (2 to 6 wt %), *Emblica officinalis* (2 to 6 wt %) and *Commiphora mukul* (2 to 6 wt %), Shilajit 1 to 4 wt %), Muktasukti bhasma (≤2 wt %), Loha bhasma (≤2 wt %), Abhraka bhasma (≤3 wt %), Swarnamaksika bhasma (≤2 wt %) and Pravala bhasma (≤2 wt %).

In another embodiment, the formulation further includes at least one of *Embelia ribes, Rubia cordifolia, Nardostachys jatamansi, Terminalia chebula, Terminalia bellerica, Piper longum, Piper nigrum, Zingiber officinalis, Boerhavia*

*diffusa, Bamboo manna, Madhuka indica, Azhadirachta indica, Picrorhiza kurroa, Holy basil, Steriospermum suaveolens, Premna mucronata, Gmelina arborea, Aegle marmelos, Oroxylum indicum, Desmodium gangeticum, Uraria picta, Solanum indicum, Solanum xanthocarpum* and *Tribulus terrestris*, preferably in an amount of ≤4 wt %

Further, the amount of gum acacia may be any amount suitable to perform the activity of an excipient. In an embodiment, the formulation may include gum acacia in the range of 0 to 50 mg per 500 mg of the formulation, preferably 10 wt %.

However, it is apparent that slight variations in the amount of the ingredients may be performed without otherwise deterring from the intended function of the herbo-mineral formulation.

The herbo-mineral formulation disclosed herein may be formulated in various dosage forms such that it is suitable for oral administration. The herbo-mineral formulation may be in the form of powder, tablets, pellets, lozenges, granules, capsules, solutions, emulsions, suspensions, or any other form suitable for use. In an embodiment, the herbo-mineral formulation is formulated in the form of powder suitable for oral administration. In another embodiment, the herbo-mineral formulation is formulated in the form of tablets, preferably 500 mg tablets. For example: Table 1 depicts the quantities of each ingredient in a 500 mg tablet.

Further disclosed herein, is a tablet for treating/preventing CVDs and related complications. In an embodiment, the tablet is a 500 mg tablet having herb component, mineral component and an excipient as depicted in Table 1.

TABLE 1

Each 500 mg tablet includes:

| S. NO. | SANSKRIT NAME | BOTANICAL/ SCIENTIFIC NAME | QUANTITY |
|---|---|---|---|
| 1 | Arjuna dry stem bark | *Terminalia arjuna* | 50 mg |
| 2 | Bala dry root | *Sida rombifolia* | 20 mg |
| 3 | Ashvagandha dry root | *Withania somnifeera* | 20 mg |
| 4 | Guduchi dry stem | *Tinospora cordifolia* | 20 mg |
| 5 | Dadima dry fruit pericarp | *Punica granatum* | 20 mg |
| 6 | Vidanga dry fruit | *Embelia ribes* | 10 mg |
| 7 | Manjishtha dry root | *Rubia cordifolia* | 10 mg |
| 8 | Jatamamsi dry root | *Nardostachys jatamansi* | 10 mg |
| 9 | Amalaki dry fruits | *Emblica officinalis* | 20 mg |
| 10 | Hareetaki dry fruits | *Terminalia chebula* | 10 mg |
| 11 | Vibhitaki dry fruits | *Terminalia bellerica* | 10 mg |
| 12 | Pippali dry fruit | *Piper longum* | 10 mg |
| 13 | Maricha dry fruit | *Piper nigrum* | 10 mg |
| 14 | Shunthi dry rhizome | *Zingiber officinalis* | 10 mg |
| 15 | Punarnava dry root | *Boerhavia diffusa* | 10 mg |
| 16 | Vamshalochana exudate | *Bamboo manna* | 10 mg |
| 17 | Madhuka dry flower | *Madhuka indica* | 10 mg |
| 18 | Nimba dry bark | *Azhadirachta indica* | 10 mg |
| 19 | Katuki dry root | *Picrorhiza kurroa* | 10 mg |
| 20 | Tulasi dry leaves | *Holy basil* | 10 mg |
| 21 | Guggulu oleo gum resin | *Commiphora mukul* | 20 mg |
| 22 | Patala dry root | *Steriospermum suaveolens* | 10 mg |
| 23 | Agnimantha dry root | *Premna mucronata* | 10 mg |
| 24 | Gambhari dry root | *Gmelina arborea* | 10 mg |
| 25 | Bilva dry root | *Aegle marmelos* | 10 mg |
| 26 | Shyonaka dry root | *Oroxylum indicum* | 10 mg |
| 27 | Shalaparni dry plant | *Desmodium gangeticum* | 10 mg |
| 28 | Prshniparni dry plant | *Uraria picta* | 10 mg |
| 29 | Brhati dry root | *Solanum indicum* | 10 mg |
| 30 | Kantakari dry plant | *Solanum xanthocarpum* | 10 mg |
| 31 | Gokshura dry fruit | *Tribulus terrestris* | 10 mg |
| 32 | Muktasukti bhasma | Incinerated Pearle oyster | 05 mg |
| 33 | Loha bhasma | Incinerated Iron | 05 mg |
| 34 | Abhraka bhasma | Incinerated Mica | 10 mg |

TABLE 1-continued

Each 500 mg tablet includes:

| S. NO. | SANSKRIT NAME | BOTANICAL/ SCIENTIFIC NAME | QUANTITY |
|---|---|---|---|
| 35 | Swarnamaksika bhasma | Incinerated Copper pyrite | 05 mg |
| 36 | Pravala bhasma | Incinerated Coral | 05 mg |
| 37 | Shilajatu fossil resin | Asphaltum | 10 mg |
|  | Excipient | *Gum acacia* | 50 mg |

Embodiments of the disclosed herbo-mineral formulation (also referred to as 'drug' or 'test drug') in tablet form were analyzed for phytoconstituents, physicochemical etc, by methods generally known in the field. The analysis and results obtained are included hereunder as examples by way of illustration only, and should not be construed to limit the scope of the claims provided herewith. It will be apparent to those skilled in the art that many modifications, both to materials and methods, may be practiced without departing from the scope of the claims.

Example 1

Physico-chemical investigation: Physicochemical investigations like Ash value, tablet hardness, disintegration time, alcohol soluble extractive value and chloroform soluble extractive values were analyzed as per the parameters given in Indian Pharmacopeia of Ayurveda. The tablet disintegration time was checked with the help of Tablet disintegration machine (I.P.Std.Rotek) and Tablet hardness tester (Secor.India) used to find out the hardness of the tablet. Each experiment was repeated thrice. Table 2 depicts the results of Physiochemical analysis.

TABLE 2

| TEST PARAMETERS | SPECIFICATIONS |
|---|---|
| Description | Dark brown colored biconvex discs |
| Identification | Positive for Iron, Calcium |
| Average weight | 500 mg ± 12.5 mg |
| Uniformity of weight | ±2.5% of actual average weight |
| Tablet hardness | 3.6 kg/cm$^2$ |
| Loss on drying | 6.2% w/w |
| Methanol soluble extractive | 41.2% w/v |
| Chloroform soluble extractive | 12.0% w/v |
| Ash value | 15.2% w/w |
| Average Disintegration time | 26 minutes |
| ASSAY | Each tablet contains, Iron - 4.5 mg, Calcium - 15 mg |

Example 2

Phyto constituents study: Tests were performed to screen the various phyto constituents such as glycosides, steroids, saponins, proteins, tannins etc.

Table 3 depicts the results of Qualitative analysis performed for phyto constituents. The test showed the presence of alkaloids, steroids, glycosides etc which could make the drug capable of curing diseases.

TABLE 3

| Test for | Aqueous Extract | Methanol Extract | Ethanol Extract |
|---|---|---|---|
| Proteins | − | − | + |
| Carbohydrates | + | + | + |
| Phenols | − | − | − |
| Tannins | ++ | ++ | ++ |
| Flavonoids | ++ | ++ | ++ |
| Saponins | + | + | + |
| Terpenoids | − | − | + |
| Glycosides | + | + | + |
| Steroids | − | + | + |
| Alkaloids | + | + | + |

(+) denotes presence and
(−) denotes absence

Method

Disclosed herein are embodiments of a method of preparing the herbo-mineral formulation. In an embodiment, the method includes:

- levigating bhasmas and shilajit in a grinder;
- adding finely powdered herbs into the grinder; and
- adding grinding decoction while continuing grinding to obtain a ground mass.

The bhasmas include at least one of Muktasukti bhasma, Loha bhasma, Abhraka bhasma, Swarnamaksika bhasma and Pravala bhasma. The mixture of bhasmas and Shilajit may be in semi solid form. In an embodiment, the levigation may be performed for a duration of around 3 hours.

Further, the finely powdered herbs include finely powdered stem bark of *Terminalia arjuna*, root of *Sida rombifolia*, root of *Withania somnifera*, root of *Rubia cordifolia*, root of *Nardostachys jatamansi*, root of *Boerhavia diffusa*, root of *Picrorhiza kurroa*, root of *Steriospermum suaveolens*, root of *Premna mucronata*, *Gmelina arborea*, root of *Aegle marmelos*, root of *Oroxylum indicum*, root of *Solanum indicum*, fruit of *Embelia ribes*, fruit of *Emblica officinalis*, fruit of *Terminalia chebula*, fruit of *Terminalia bellerica*, fruit of *Piper longum*, fruit of *Piper nigrum*, fruit of *Tribulus terrestris*, bark of *Azhadirachta indica*, plant of *Solanum xanthocarpum*, plant of *Uraria picta*, plant of *Desmodium gangeticum*, stem of *Tinospora cordifolia*, fruit pericarp of *Punica granatum*, rhizome of *Zingiber officinalis*, exudate of Bamboo manna, flower of *Madhuka indica*, leaves of Holy basil and gum resin of *Commiphora mukul*.

The grinding decoction is a decoction of selected herbs (also referred as grinding herbs). In an embodiment, the grinding decoction is a decoction of one or more grinding herbs selected from a group consisting of: *Terminalia arjuna, Asparagus racemosus, Asafetida, Cuminum cyminum, Plumbago rosea, Baliospermum montanum, Ocimum sanctum, Aloe vera, Plantago ovata, Steriospermum suaveolens, Premna mucronata, Gmelina arborea, Aegle marmelos, Oroxylum indicum, Desmodium gangeticum, Uraria picta, Solanum indicum, Solanum xanthocarpum* and *Tribulus terrestris*.

The decoction may be obtained by any method of decocting generally known in the field. In an embodiment, the method of preparation of grinding decoction includes, soaking the grinding herbs; for example: soaking powdered dry bark of *Terminalia arjuna*, fresh root of *Asparagus racemosus*, resin Asafetida, dry fruit of *Cuminum cyminum*, dry root of *Plumbago rosea*, dry root of *Baliospermum montanum*, dry leaves of *Ocimum sanctum*, fresh leaves of *Aloe vera*, dry seeds of *Plantago ovata*, dry roots of *Steriospermum suaveolens*, dry roots of *Premna mucronata*, dry root of *Gmelina arborea*, dry root of *Aegle marmelos*, dry root of *Oroxylum indicum*, dry plant of *Desmodium gangeticum*, dry plant of *Uraria picta*, dry root of *Solanum indicum*, dry plant of *Solanum xanthocarpum* and dry fruit of *Tribulus terrestris*, and concentrating the soaked herb mixture.

In an embodiment, soaking may be performed by soaking the grinding herbs in 16 parts of water overnight. In a further embodiment, concentrating may be performed by boiling at high temperature, preferably about 80° C. to 85° C., until ⅛th of the liquid remains. Concentration may be confirmed with the help of Brix meter.

Figure 2:
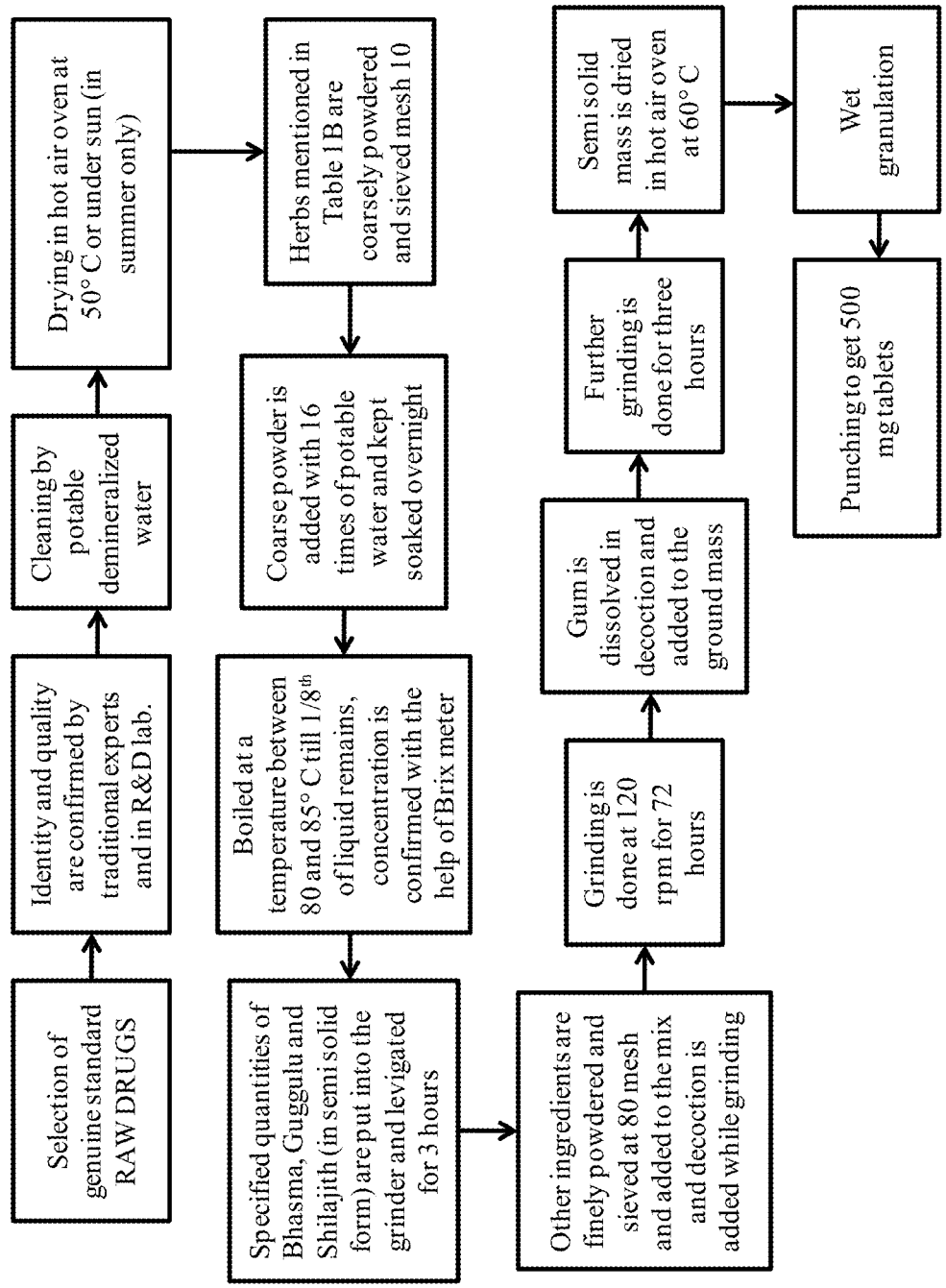
FIG. 2 depicts a flowchart for the preparation of fortified tablets.

Further, once the grinding decoction is added, grinding is continued. In an embodiment, grinding is continued for about 72 hours, preferably at 120 rpm, to obtain a ground mass. In an embodiment, the method of preparation may further include adding excipient to the ground mass, wherein gum acacia may be added to the ground mass by dissolving in the grinding decoction, while continuing grinding for 3 hours to obtain a semisolid mass. The method of preparation may further include drying at 50° C.-60° C., preferably in a hot air oven; wet granulating; and punching to obtain 500 mg tablets. FIG. 2 depicts a flowchart for the preparation of fortified tablets. Table 4 depicts an embodiment of the Herbs required for grinding (grinding herbs).

TABLE 4

List of grinding herbs
Decoction of following herbs:

| 1 | Arjuna dry bark | Terminalia arjuna | 1 part |
|---|---|---|---|
| 2 | Shatavari fresh root | Asparagus racemosus | 1 part |
| 3 | Hingu resin | Asafetida | 1 part |
| 4 | Jeeraka dry fruit | Cuminum cyminum | 1 part |
| 5 | Chitraka dry root | Plumbago rosea | 1 part |
| 6 | Danti dry root | Baliospermum montanum | 1 part |
| 7 | Tulasi dry leaves | Ocimum sanctum | 1 part |
| 8 | Kumari fresh leaf | Aloe vera | 1 part |
| 9 | Ishvaragola dry seeds | Plantago ovata | 1 part |
| 10 | Patala dry root | Steriospermum suaveolens | 1 part |
| 11 | Agnimantha dry root | Premna mucronata | 1 part |
| 12 | Gambhari dry root | Gmelina arborea | 1 part |
| 13 | Bilva dry root | Aegle marmelos | 1 part |
| 14 | Shyonaka dry root | Oroxylum indicum | 1 part |
| 15 | Shalaparni dry plant | Desmodium gangeticum | 1 part |
| 16 | Prshniparni dry plant | Uraria picta | 1 part |
| 17 | Brhati dry root | Solanum indicum | 1 part |
| 18 | Kantakari dry plant | Solanum xanthocarpum | 1 part |
| 19 | Gokshura dry fruit | Tribulus terrestris | 1 part |
|  | Jala | Water | 304 parts |
|  | Avashesha |  | ⅛ part of water |

The bhasmas that are used in the various embodiments of the disclosed herbo-mineral formulation may be prepared by methods that are generally known in the field. Bhasmas may be prepared by selecting genuine standard minerals as starting material such as Swarnamakshika, Mica, Iron, pearl oyster etc; drying in a hot air oven; purifying the mineral by triturating, quenching, boiling, etc; triturating with herbal decoction; preparing into discs; drying of discs; preparing sharavasam puta, subjecting Sharavasam puta to Gaja puta, and powdering of discs once cooled. As is generally known in the field, once the disc is powdered, the powder may again be subjected to many repetitions of trituration with herbal decoction followed by preparing into discs; drying of discs; preparing sharavasam puta, subjecting Sharavasam puta to Gaja puta, and powdering, until bhasma is obtained. The number of repetitions may vary from 0 to 30 times. In an embodiment, the method is repeated as many as 30 times till bhasma is obtained.

The starting materials used in the preparation of bhasmas may include standard minerals generally used in the field. In an embodiment, the preparation of Swarna Makshika Bhasma includes swarna makshika as the starting material. FIG. 1(a) depicts a flowchart for the preparation of Swarna Makshika Bhasma using swarna makshika as the starting material.

Figure 1B:
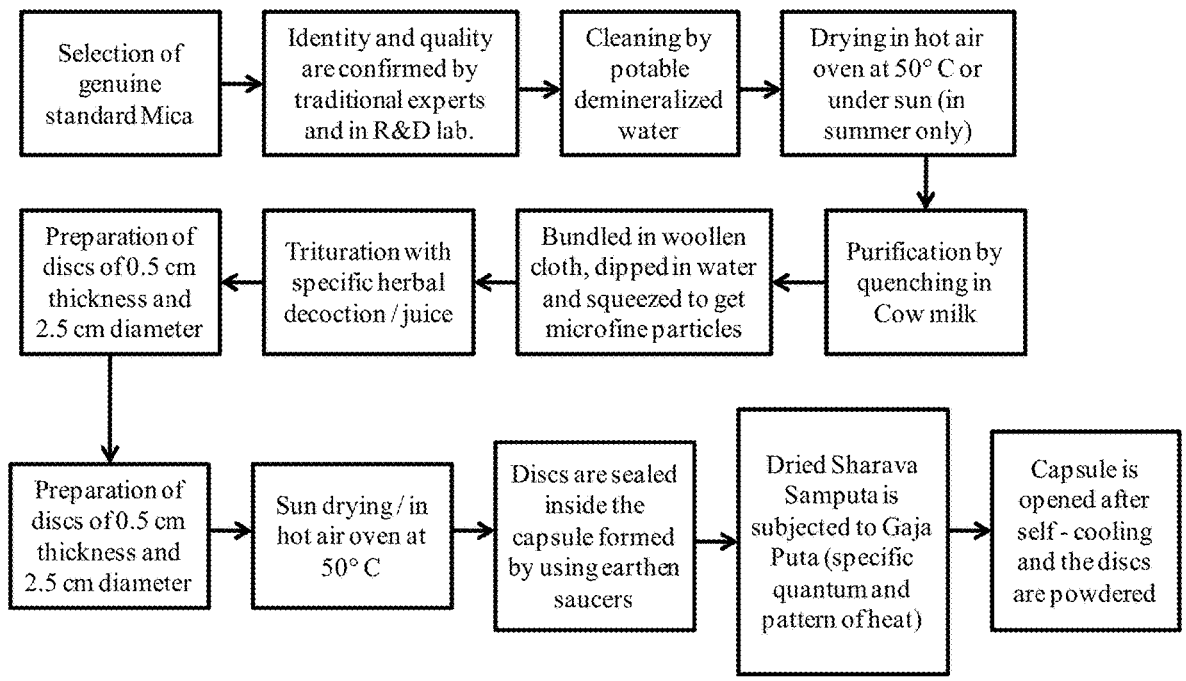
FIG. 1(b) depicts a flowchart for the preparation of Abhraka Bhasma.
Figure 1C:
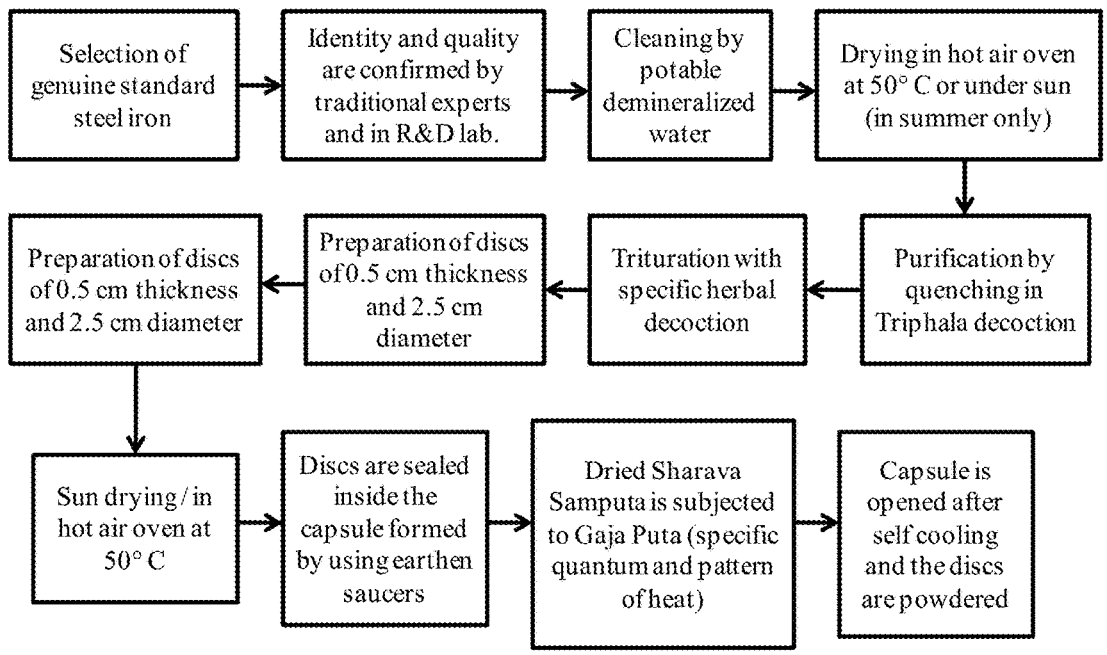
FIG. 1(c) depicts a flowchart for the preparation of Loha Bhasma.
Figure 1D:
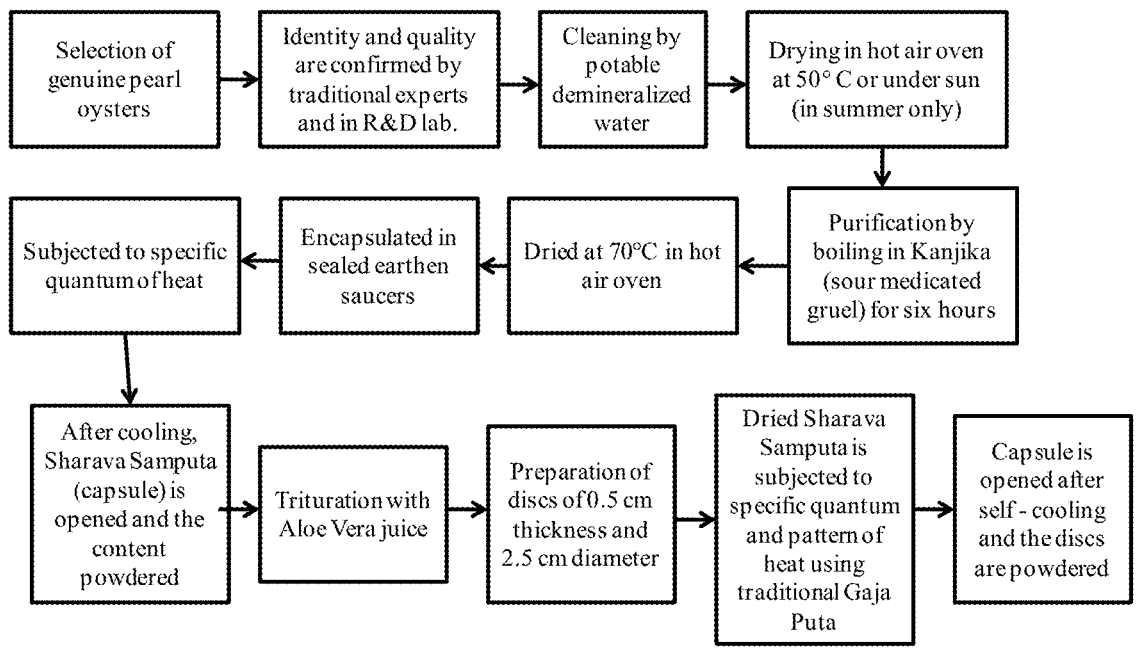
FIG. 1(d) depicts a flowchart for the preparation of Mukta sukti Bhasma.
Figure 1E:
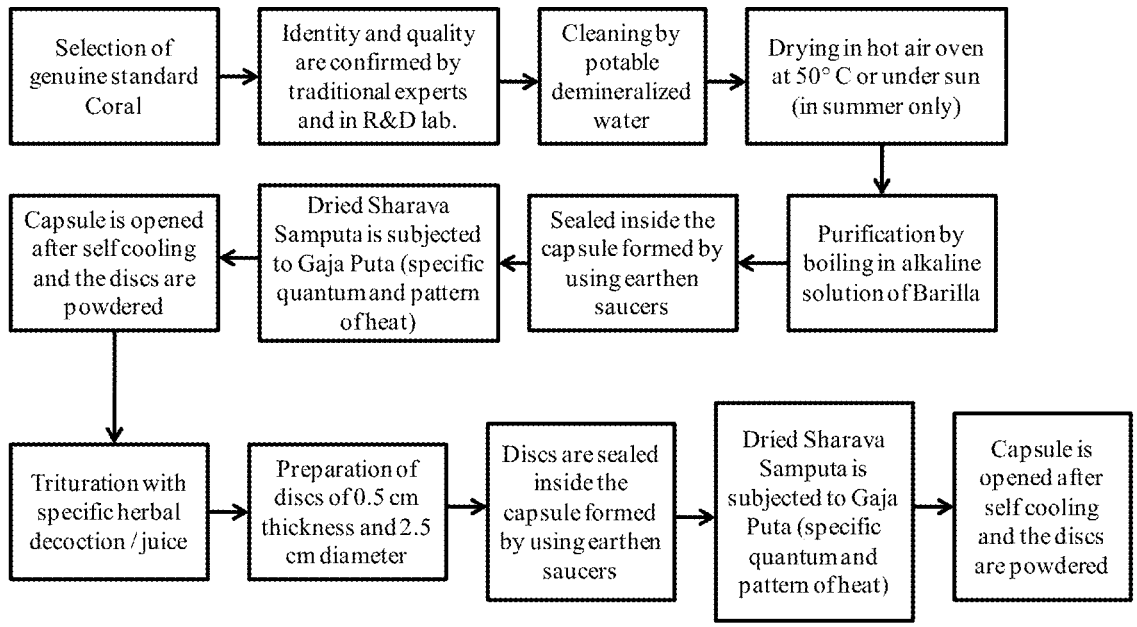
FIG. 1(e) depicts a flowchart for the preparation of Pravala Bhasma.

In another embodiment, the preparation of Abhraka Bhasma includes Mica as the starting material. FIG. 1(b) depicts a flowchart for the preparation of Abhraka Bhasma using Mica as the starting material. In an embodiment, the preparation of Loha Bhasma includes steel iron as the starting material. FIG. 1(c) depicts a flowchart for the preparation of Loha Bhasma using steel iron as the starting material. Further, in an embodiment, the preparation of Muktasukti Bhasma includes pearl oyster as the starting material. FIG. 1(d) depicts a flowchart for the preparation of Muktasukti Bhasma using alloys of Pearl oyster as the starting material. In an embodiment, the preparation of Pravala Bhasma includes Coral as the starting material. FIG. 1(e) depicts a flowchart for the preparation of Pravala Bhasma using Coral as the starting material.

In an embodiment, purification of mineral includes mixing the mineral with rocksalt and lemon juice and heating strongly till partially oxidized into reddish powder which is further be used in the preparation of Swarna makshika Bhasma. In another embodiment, purification of mineral includes quenching of mineral in Cow's milk wherein it is further used in the preparation of Abhraka Bhasma.

In yet another embodiment, purification of mineral includes quenching of mineral in Triphala decoction which is further used in the preparation of Loha Bhasma. In yet another embodiment, purification of mineral includes quenching of mineral in Kanjika (sour medicated gruel) which is further used in the preparation of Mukta sukti Bhasma.

Further, in an embodiment, purification of mineral includes boiling the mineral in alkaline solution of Barilla which is further used in the preparation of Pravala Bhasma.

The herbal decoction used may be any herbal decoction that is generally used for triturating in the preparation of bhasmas. In an embodiment, the herbal decoction includes at least one of Nimbu Swarasa (Lemon juice) and Kulatha Kwatha (Decoction of Dolichos biflorus), wherein it is useful in the preparation of Swarna Makshika bhasma. In another embodiment, the herbal decoction includes at least one of Arka Ksheera (Latex of calotropes procera), Snuhi Ksheera (Latex of Euphorbia neriifolia), Vata Ksheera (Latex of Ficus bengalensis), Kakamachi Rasa (fresh juice of *Solanum nigrum* whole plant), Gokshura Kwatha (decoction of *tribulus terrestris* fruits), Apamarga Rasa (Juice of Achyranthus aspera plant), Vata Praroha Swarasa (juice of aerial root of Ficus bengalensis), Gomutra (Cow urine), Tulasi Swarasa (Fresh juice of *Ocimum sanctum* leaves), Kadali Shipha Jala (Juice of plantain rhizome), Eranda patra rasa (Juice of Ricinus communis leaves), and Guda (Jaggery), wherein it is useful in the preparation of Abhraka Bhasma. In an embodiment, the herbal decoction includes Triphala Kashaya (decoction of fruits of *Terminalia chebula, Terminalia bellerica* and *Emblica officinalis*), wherein it is useful in the preparation of Loha Bhasma. In an embodiment, the herbal decoction includes *Aloe Vera* juice, wherein it is useful in the preparation of Muktasukti Bhasma. In another embodiment, the herbal decoction includes at least one of *Aloe vera* (fresh juice of leaves), Sesbania seban (fresh juice of leaves), *Asparagus racemosus* (fresh juice of roots) and Cow milk, wherein it is useful in the preparation of Pravala Bhasma.

Treatment

Disclosed herein are embodiments of a method of treating/preventing Cardio vascular diseases. Also disclosed are embodiments of a method of reducing the risks of CVD.

In an embodiment, the method includes administering to a patient a composition having a herb component, a mineral component and a suitable excipient, wherein the herb component includes the herbs *Terminalia arjuna* (8 to 12 wt %), *Sida rombifolia* (2 to 6 wt %), *Withania somnifera* (2 to 6 wt %), *Tinospora cordifolia* (2 to 6 wt %), *Punica granatum* (2 to 6 wt %), *Emblica officinalis* (2 to 6 wt %), *Commiphora mukul* (2 to 6 wt %) and at least one herb selected from the group consisting of *Terminalia arjuna, Sida rombifolia, Withania somnifera, Tinospora cordifolia, Punica granatum, Embelia ribes, Rubia cordifolia, Nardostachys jatamansi, Emblica officinalis, Terminalia chebula, Terminalia bellerica, Piper longum, Piper nigrum, Zingiber officinalis, Boerhavia diffusa, Bamboo manna, Madhuka indica, Azhadirachta indica, Picrorhiza kurroa, Holy basil, Commiphora mukul, Steriospermum suaveolens, Premna mucronata, Gmelina arborea, Aegle marmelos, Oroxylum indicum, Desmodium gangeticum, Uraria picta, Solanum indicum* and *Solanum xanthocarpum*; and the mineral component includes Shilajit (1 to 4 wt %), and at least on of Muktasukti bhasma ($\leq 2$ wt %), Loha bhasma ($\leq 2$ wt %), Abhraka bhasma ($\leq 3$ wt %), Swarnamaksika bhasma ($\leq 2$ wt %) and Pravala bhasma ($\leq 2$ wt %).

In an embodiment, the patient may be any individual in need of such treatment including ones having/suspected of having Cardiovascular diseases. Further, the patient may also be any individual having/suspected of having any complication associated with heart and blood vessels. In an embodiment, Cardio vascular diseases include cardiac arrhythmias, ischemic heart diseases, coronary artery disease, valve defects, mitral valve prolapse etc. Further, the patient may also be any individual prone to or having risks of Cardiovascular diseases, for example: individuals having hypertension, obesity, increased blood sugar, etc.

In an embodiment, the method of treating/preventing CVD includes administering the Disclosed formulation to a patient wherein the disclosed formulation acts as at least one of anti-oxidating, anti-stress, hypolipidemic, atherogenic, antihypertensive, apoptotsis inhibiting and cardio-protective agent.

The disclosed method of treatment may be used as a primary line of treatment or as an adjunct to other CVD treatment methods. In an embodiment, the method may be instrumental in improving the health conditions of individuals having CVD.

The dosage of the test drug and the treatment regimen may vary depending on the patient. The disclosed formulation was subjected to acute oral toxicity study, and a study to check its effect on behavior and nervous system. The studies proved that Test drug is free from toxicity even at a dose of 6000 mg/kg weight which was the maximum possible dose. It was also found to have no harmful effects on behavior and nervous system.

The Disclosed formulation (also referred as Test drug or Test product) was further evaluated for efficacy of cardio-protective activity by preclinical and clinical studies, as described hereunder by way of examples. Embodiments of the formulation disclosed herein is further described by reference to the following examples by way of illustration only, and should not be construed to limit the scope of the embodiments herein. It will be apparent to those skilled in the art that many modifications, both to materials and methods, may be practiced without departing from the scope of the claims.

Example 3

Preclinical Study

The aim of this study was to analyze the Cardioprotective activity of test product on Isoproterenol (ISP) induced experimental model of myocardial infarction. The effect of Test drug on the membrane bound enzymes like Na+K+ATPase, Ca2+ATPase and Mg2+ATPase were investigated. The action of Test drug on apoptotic and pre-apoptotic markers gene expression in ISP induced myocardial infarction was analyzed. Also, the effect of Test drug on CK-MB activity and oxidative stress markers was evaluated.
Experiment Details:
Animals: 35 male Sprague-Dawley rats of 150-200 g body weight were selected for the study. Animals were housed in individual polycarbonate cages in a well-ventilated room under an ambient temperature of 23±2 degree C. and 40-65% relative humidity, with artificial photoperiod 12-h light/12-h dark cycle. They were provided with standard rodent pellet diet (Nutrilab Rodent, Tetragon Chemie, India) and purified water ad libitum (RIOS, USA). Experimental animals were acclimatized for 7 days to the laboratory conditions prior to experimentation. The study protocol was approved by Institutional Animal Ethical Committee (IAEC).

Experimental groups and design: Rats were randomized into 5 groups based on the body weight. ISP (120 mg/kg) was injected subcutaneously to rats on 19th and 21st day to induce experimental myocardial infarction. Test drug was orally administered throughout the study.
Group I (Normal control): 0.5% CMC
Group II (Positive control): 0.5% CMC+ISP (120 mg/kg)
Group III (Standard): Carvedilol (2 mg/kg/day, p.o)+ISP (120 mg/kg, s.c.)
Group IV (Low dose): Test drug (50 mg/kg/day, p.o)+ISP (120 mg/kg, s.c.)
Group V (High dose): Test drug (100 mg/kg/day, p.o)+ISP (120 mg/kg, s.c.)

The change in body weight was recorded every week. At the end of the experiment, blood was collected and the plasma was separated for biochemical investigation. The animals were euthanized and the organs (heart, Kidney and adrenals) were dissected out and weighed. Heart homogenate was used for further analysis and LV was separated for the analysis of apoptotic marker gene expression as depicted in the various examples hereunder.
Biochemical Parameters Example 3(a)

CK-MB (Creatinine Kinase-MB)

Figure 3:
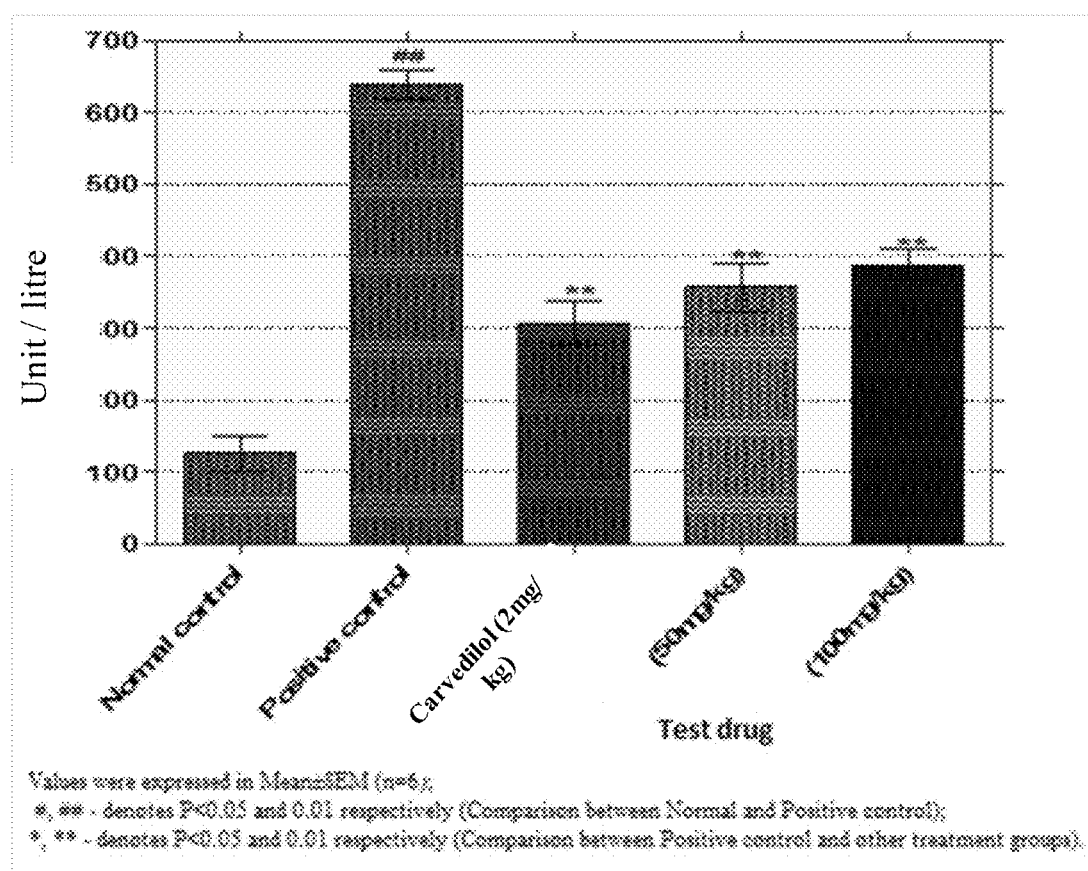
FIG. 3 depicts the effect of Test Drug on CK-MB activity.

The CK-MB activity was measured by kit method (Spinreact, Spain) using Semi-automated biochemical analyzer.
Effect of Test Drug on CK-MB Activity:
FIG. 3 depicts CK-MB activity. Rats induced with ISP showed significant elevation ($P<0.01$) in CK-MB activity when compared to normal rats, whereas pre-treatment with test drug decreased ($P<0.01$) its activity.

The serum marker enzyme CK-MB in ISP induced rats serves as the index to assess the severity of myocardial injury. This increase in activity is accompanied by their concomitant increase in wet weight of myocardium confirms the onset of apoptotic pathway. Extent of cardio-protection offered by the drug is associated with the significant attenuation of CK-MB activity. Hence, pretreatment with Test Drug significantly possess cardio-protective effect and maintains myocardial membrane integrity.

Example 3(b)

Na+K+ATPase

Reagents
1. Tris HCl (184 mM) pH-7.5: 1.449 g in 50 ml of distilled water
2. KCl (50 mM): 37.275 mg in 10 ml of distilled water
3. Sodium EDTA (1 mM): 4 mg in 10 ml of distilled water
4. NaCl (600 mM): 350.64 mg in 10 ml. of distilled water
5. 10% TCA: 10 g in 100 ml of distilled water
6. 15% sodium meta bisulphate: 7.5 g in 50 ml of distilled water
7. 20% sodium sulphate: 2 g in 10 ml of distilled water
8. 5N H2SO4: 13.5 ml of H2SO4 in 100 ml of distilled water
9. Ammonium molybdate (2.5%): 2.5 g in 100 ml of 5N Sulphuric acid
10. ANSA (0.1%): 100 mg in 39 ml of 15% sodium meta bisulphate. Then 1 ml of 20% sodium sulphite was added and the volume was made up to 100 ml with distilled water.

Protocol: Na+K+ATPase was assayed by taking 250 µl of tris HCl buffer followed by the addition of 50 µl of 600 mM NaCl, 50 µl of 50 mM KCL, along with 50 µl of 1 mM Na. EDTA, and 50 µl of 80 mM ATP. The reaction mixture was pre-incubated at 37° C. for 10 mins. Then 25 µl of 10% homogenate was added to the test alone and further incubated at 37° C. for 1 hr. The reaction was immediately arrested by the addition of 10% TCA. The control reaction rate was correspondingly assessed by adding 25 µl of 10% homogenate only after arresting the reaction. The precipitate was removed by centrifugation at 3500 rpm for 10 minutes. To 50 µl of the supernatant, 1075 µl of distilled water, 125 µl of Ammonium molybdate and 50 µl of ANSA were added and incubated for 10 mins at 37° C. The intensity of blue colour was read at 640 nm using spectrophotometer against a blank that contained all the reagents minus the supernatant. The results are expressed in µg of Pi liberated/min/mg of protein.

Figure 4:
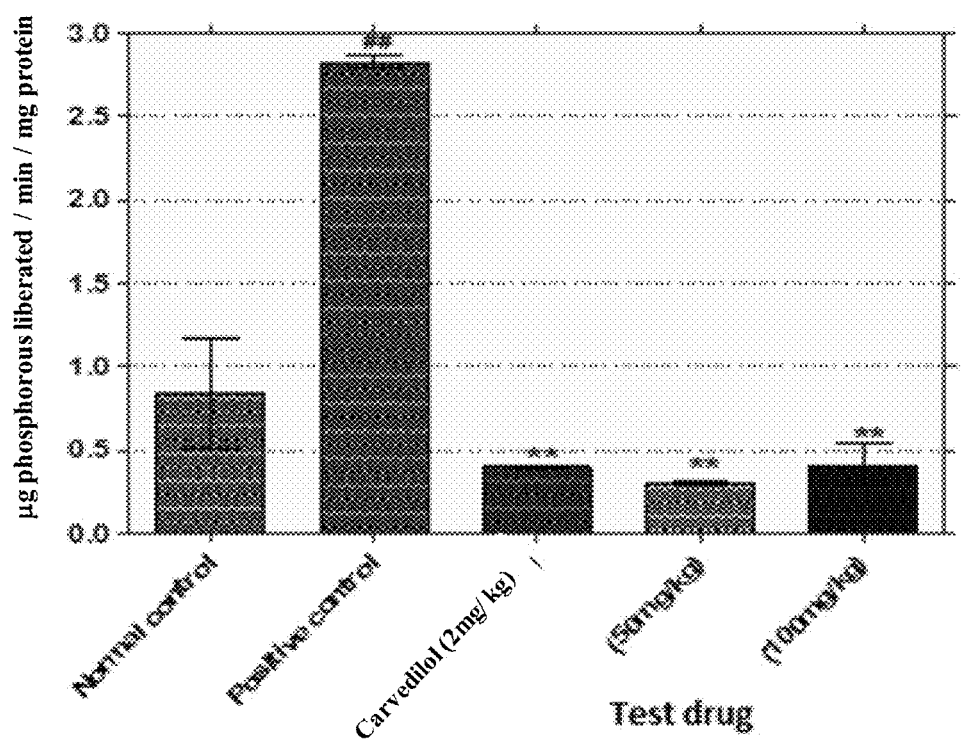
FIG. 4 depicts the effect of Test Drug on Na+K+ATPase.

Effect of Test Drug on Membrane Bound Enzymes: $Na^+K^+$ATPase:

FIG. 4 depicts $Na^+K^+$ATPase activity. It was observed that ISP induced rats showed significant ($P<0.01$) decrease in $Na^+ K^+$ ATPase. Whereas, pretreatment with Test drug (50 and 100 mg/kg) showed significant ($P<0.01$) elevation in $Na^+K^+$ ATPase activity irrespective of the doses.

$Na^+ K^+$ ATPase, a membrane bound enzyme is responsible for sodium ion influx and potassium ion reflex during muscle contraction and relaxation. Induction of myocardial infarction with ISP inhibited the influx of sodium ions thereby hindering the contraction and relaxation of the heart muscle. Pretreatment with Test drug was comparable with the reference drug, carvedilol in enhancing the Na$^+$K$^+$ ATPase activity Example 3(c)

Mg2+ ATPase

Reagents:
1. Tris HCl (0.1M) pH-7.4: 1.576 g in 100 ml of distilled water
2. KCl (0.1M): 74.55 mg in 10 ml of distilled water
3. MgCl2 (0.1M): 200 mg in 10 ml of distilled water
4. ATP (80 mM): 440 mg in 10 ml of distilled water
5. 10% TCA: 10 g in 100 ml of distilled water
6. 15% sodium meta bisulphate: 7.5 g in 50 ml of distilled water
7. 20% sodium sulphate: 2 g in 10 ml of distilled water
8. 5N H2SO4: 13.5 ml of H2SO4 in 100 ml of distilled water
9. Ammonium molybdate (2.5%): 2.5 g in 100 ml of 5N Sulphuric acid.
10. ANSA (0.1%): 100 mg in 39 ml of 15% sodium meta bisulphate. Then 1 ml of 20% sodium sulphite was added and the volume was made up to 100 ml with distilled water.

Protocol: Total ATPase was assayed by taking 0.75 ml of tris HCL buffer followed by the addition of 50 µl of 100 mM KCl, along with 50 µl of 100 mM MgCl$_2$, and 50 µl of 80 mM ATP. The reaction mixture was pre-incubated at 37° C. for 2 mins. Then 50 µl of 10% homogenate was added to the test alone and further incubated at 37° C. for 20 mins. The reaction was immediately arrested by the addition of 500 µl of 10% TCA. Control reaction rate was correspondingly assessed by adding 50 µl of 10% homogenate only after arresting the reaction. The precipitate was removed by centrifugation at 3500 rpm for 10 minutes. To 50 µl of the supernatant, 1075 µl of distilled water, 125 µl of Ammonium molybdate and 50 µl of ANSA were added and incubated for 10 mins at 37° C. The intensity of blue colour was read at 640 nm using spectrophotometer against a blank that contained all the reagents minus the supernatant. The results are expressed in µg of Pi liberated/min/mg of protein.

Figure 5:
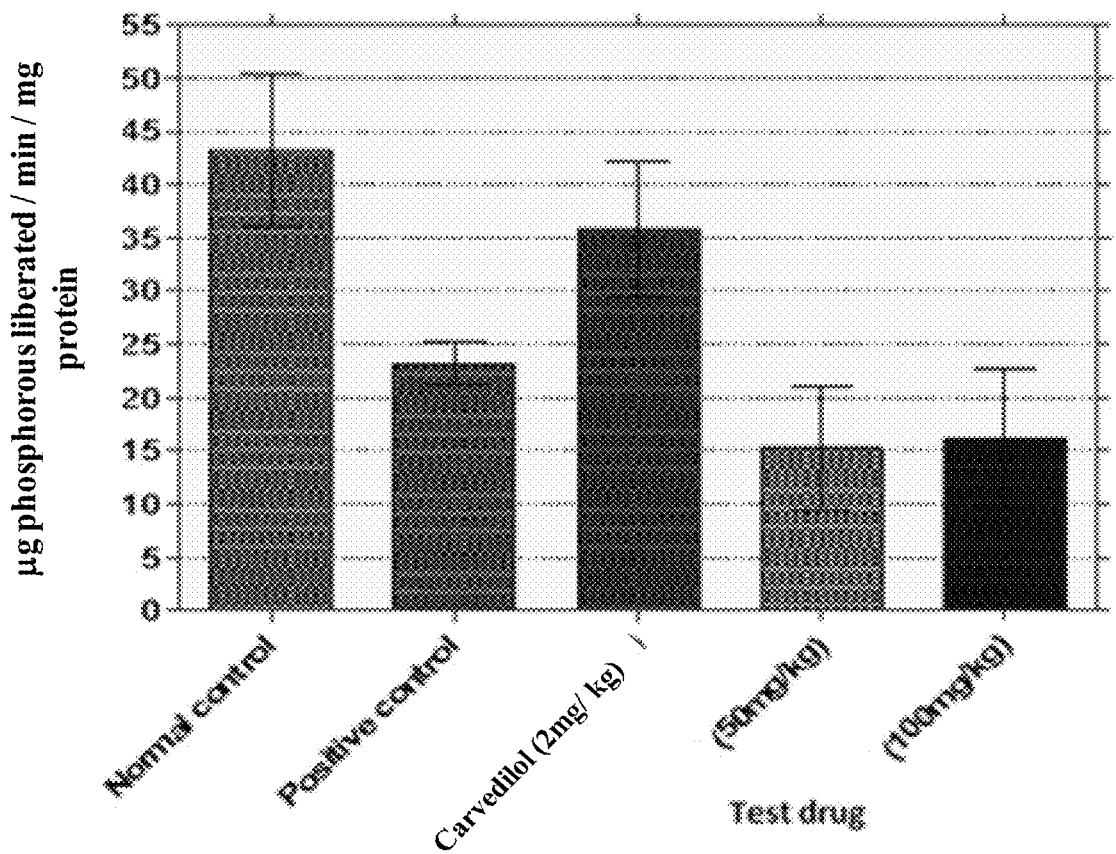
FIG. 5 depicts the effect of Test Drug on Mg2+ATPase.

Effect of Test Drug on Membrane Bound Enzymes: Mg$^{2+}$ ATPase:

FIG. 5 depicts Mg$^{2+}$ATPase activity. It was observed that ISP induced rats showed significant (P<0.01) decrease in Mg$^{2+}$ ATPase activity when compared to the normal control rats. Whereas, pretreatment with Test drug (50 and 100 mg/kg) showed significant (P<0.01) elevation in Mg$^{2+}$ ATPase activity irrespective of the doses. Mg$^{2+}$ ATPase regulates the intracellular Mg2+ levels. Pretreatment with Test drug was comparable with the reference drug, carvedilol in enhancing the Mg$^{2+}$ ATPase activity Example 3(d)

Ca2+ATPase

Reagents:
1. Tris HCl (0.1M) pH-7.4: 1.576 g in 100 ml of distilled water
2. KCl (0.1M): 74.55 mg in 10 ml of distilled water
3. CaCl2 (0.1M): 147.02 mg in 10 ml of distilled water
4. ATP (80 mM): 440 mg in 10 ml of distilled water
5. 10% TCA: 10 g in 100 ml of distilled water
6. 15% sodium meta bisulphate: 7.5 g in 50 ml of distilled water
7. 20% sodium sulphate: 2 g in 10 ml of distilled water
8. 5N H2SO4: 13.5 ml of H2SO4 in 100 ml of distilled water.
9. Ammonium molybdate (2.5%): 2.5 g in 100 ml of 5N Sulphuric acid.
10. ANSA (0.1%): 100 mg in 39 ml of 15% sodium meta bisulphate. Then 1 ml of 20% sodium sulphite was added and the volume was made up to 100 ml with distilled water.

Protocol: Ca$^{2+}$ ATPase was assayed by taking 0.75 ml of tris HCL buffer followed by the addition of 50 µl of 100 mM KCl, 50 µl of 100 mM CaCl$_2$ and 50 µl of 80 mM ATP. The reaction mixture was pre-incubated at 37° C. for 2 mins. Then 50 µl of 10% homogenate was added to the test alone and further incubated at 37° C. for 20 mins. The reaction was immediately arrested by the addition of 500 µl of 10% TCA. Control reaction rate was correspondingly assessed by adding 50 µl of 10% homogenate only after arresting the reaction. The precipitate was removed by centrifugation at 3500 rpm for 10 minutes. To 50 µl of the supernatant, 1075 µl of distilled water, 125 µl of Ammonium molybdate and 50 µl of ANSA were added and incubated for 10 mins at 37° C. The intensity of blue colour was read at 640 nm using spectrophotometer against a blank that contained all the reagents minus the supernatant. The results are expressed in µg of Pi liberated/min/mg of protein.

Figure 6:
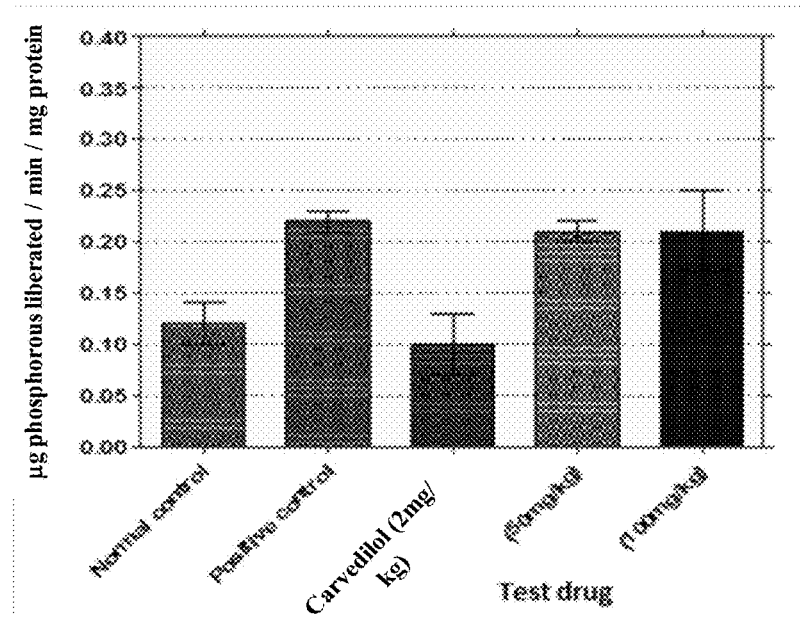
FIG. 6 depicts the effect of Test Drug on Ca2+ATPase.

Effect of Test Drug on Ca2+ATPase:

FIG. 6 depicts Ca$^{2+}$ ATPase activity. It was observed that in rats administered with ISP, Ca$^{2+}$ ATPase activity was increased when compared to normal control rats. On the other hand, pretreatment with Test drug showed reduced Ca$^{2+}$ ATPase activity and the result was independent of the dose concentration.

Intracellular calcium (Ca$^{2+}$) levels are maintained and regulated by Ca$^{2+}$ ATPase. Enhanced Ca$^{2+}$ ATPase and intracellular Ca$^{2+}$ overload in ISP-treated rats can be correlated to the action of adenylate cyclase. Phosphorylation of Ca$^{2+}$ channel protein by cAMP is expected to increase the Ca$^{2+}$ influx into the myocardium and thus burdening it. In our study, pre-supplementation with Test drug showed potent resistance to the perturbations in Ca$^{2+}$ ATPase caused due to ISP injection.

Oxidative Stress-Anti-Oxidant Potential of Test Drug on ISP Induced Myocardial Infarction Example 3(e)

Lipid Hydroperoxide (LPO)

Reagents:
1. ThioBarbituric Acid (TBA) (0.8%): 0.8 gms in 0.5N HCl
2. Butylated Hydroxyl Toluene (0.05%): 0.05 gms in methanol.
3. Saline (0.9%): 0.9 g in 100 ml distilled water Protocol: The method involved heating of 0.5 ml of heart homogenate of experimental rats with 0.8 ml saline, 0.5 ml of BHT and 3.5 ml TBA reagent for 11/2 min in a boiling water bath. After cooling, the solution was centrifuged at 2,000 rpm for 10 min and the precipitate obtained was removed. The absorbance of the supernatant was determined at 532 nm using spectrophotometer against a blank that contained all the reagents minus the biological sample. The values were expressed in mg/g tissue (Okhawa H et al., 1979).

Figure 7:
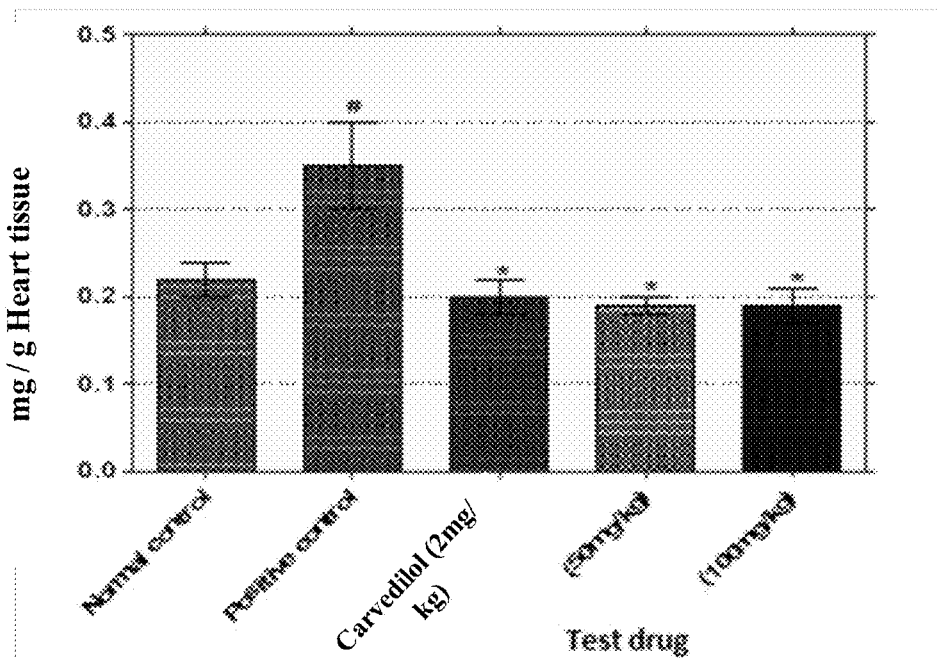
FIG. 7 depicts the effect of Test Drug on Lipid Peroxidation content.

Lipid Peroxidation (Thiobarbituric Acid Reactive Substances):

FIG. 7 depicts LPO Content. ISP induced rats showed significant increase in the levels of heart TBARS when compared to normal control rats. Pretreatment with Test drug showed considerable decrease in the levels of heart TBARS in ISP-induced rats. The results were comparable with that of standard drug, Carvedilol.

ISP treatment is known to produce free radical moieties via its quinine metabolites that react with oxygen ultimately resulting in enhanced generation of Reactive oxygen species (ROS). ROS, the highly toxic by-products of aerobic metabolism are known to react extensively with cell membranes and macromolecules enhancing formation of lipid peroxides thus leading to tissue damage. Lipid peroxidation is an important pathogenic event in myocardial necrosis and accumulation of lipid hydroperoxides reflects damage of the cardiac constituents. The increased levels of MDA, a lipid peroxidation end-product, observed in our study following isoproterenol administration might be due to free radical mediated membrane damage. Our findings suggest that TEST DRUG possess lipid peroxidation inhibitory activity.

Example 3(f)

Superoxide Dismutase (SOD)

Reagents:
1. Sodium pyrophosphate buffer (0.025M): 1.115 g in 100 ml of distilled water.
2. Phenazonium Metho Sulphate (PMS) (186 µM): 3 mg in 10 ml of distilled water (930 µM). Then 1:5 dilutions were carried out to obtain 186 µM.
3. Nitro Blue Tetrazolium (chloride) (NBT) (300 µM): 3 mg in 10 ml of phosphate buffer.
4. NADH (780 µM): 6 mg in 10 ml of phosphate buffer.

Protocol: Superoxide dismutase was assayed by taking 0.05 ml of heart homogenate followed by addition of 0.3 ml of sodium pyrophosphate buffer (0.025M, PH 8.3), 0.025 ml of PMS (186 µM) and 0.075 ml of NBT (300 µM in buffer of PH 8.3) The reaction was started by addition of 0.075 ml of NADH (780 µM in buffer of PH 8.3). After incubation at 300 C for 90 seconds, the reaction was stopped by addition of 0.25 ml glacial acetic acid. Then the reaction mixture was stirred vigorously and shaken with 2.0 ml of n-Butanol. The mixture was allowed to stand for 10 minutes and centrifuged. 1.5 ml of n-butanol alone was served as blank. The colour intensity of the chromogen was read at 560 nm (Kakkar, P., et al 1984).

Figure 8:
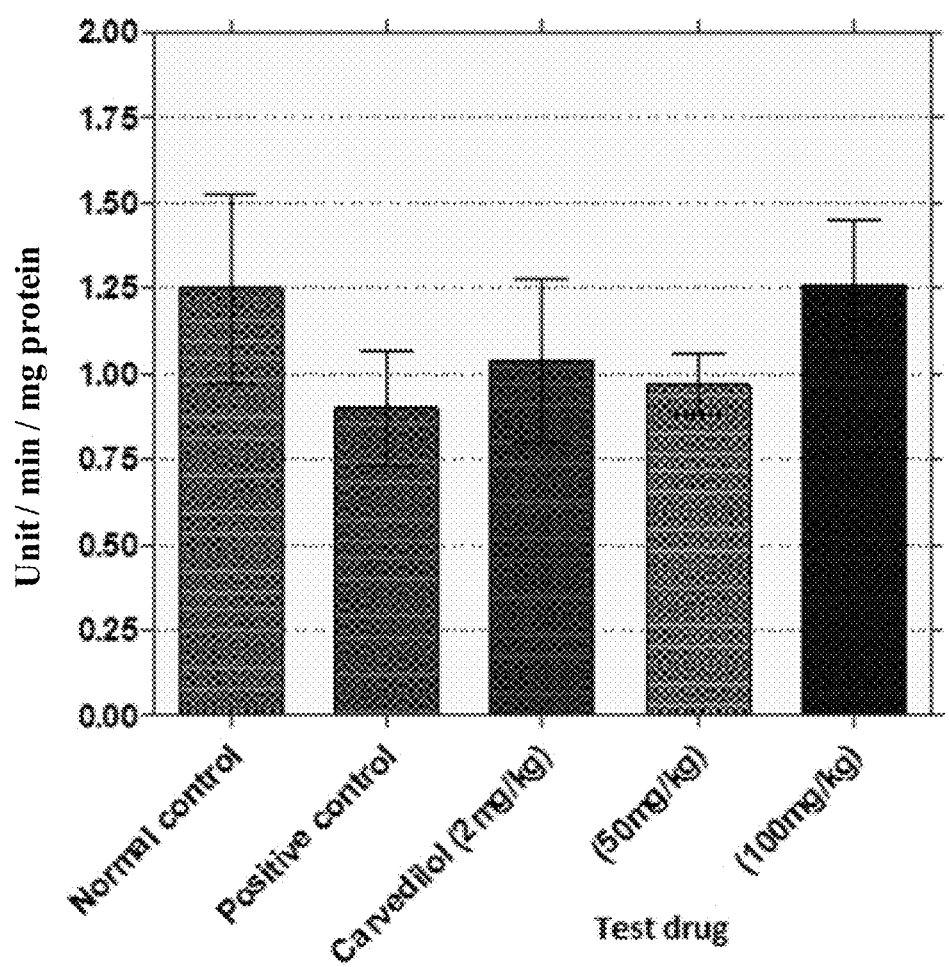
FIG. 8 depicts the effect of Test Drug on Superoxide dismutase activity.

Superoxide dismutase activity: FIG. 8 depicts SOD activity. IT was observed that Superoxide dismutase levels were decreased in ISP induced rats when compared to the normal control rats. Pretreatment with Test Drug exhibited a dose dependent increase in SOD levels when compared to vehicle treated ISP induced rats. The SOD levels of Test drug treated were comparable with that of the standard drug, Carvedilol treated rats.

Superoxide anions and other reactive oxygen species produce an oxidative environment commonly called as oxidative stress in rat myocardium. Among the free radical scavenging antioxidants SOD was considered to be the cellular defense against oxidative injury. The results envisaged that the decreased levels of SOD following ISP administration were ameliorated to a greater extend by pre-treatment with Test drug.

Example 3(g)

GSH and Glutathione Peroxidase Activity

Glutathione peroxidase [GPX]
Reagents:
1. Sodium Azide (10 mM): 16 mg in 25 ml of distilled water
2. GSH (2 mM): 30.732 mg in 50 ml of distilled water.
3. H2O2 (1 mM): 29 µl in 1000 ml of distilled water
4. 10% TCA: 10 g in 100 ml of distilled water
5. K.EDTA (0.4 mM): 16 mg in 100 ml of distilled water
6. Tris HCL Buffer (0.4 mM): 6.304 g in 100 ml of distilled water
7. DTNB (0.6 mM): 12 mg in 50 ml PO4 buffer.

Protocol: Glutathione peroxidase (GPX) was assayed by taking 200 µl of tris HCL buffer (0.4 M), 0.4 mM K.EDTA along with 100 µl of sodium azide and 200 µl of enzyme preparation (hemolysate) and mixed well. Thereafter, 200 µl of reduced glutathione solution (2 mM) followed by 0.1 ml H2O2 were added The overall reaction was arrested by adding 0.5 ml of 10% TCA. The precipitate was removed by centrifugation at 4000 rpm for 10 minutes. The absorbance was read at 412 nm using spectrophotometer. The non-enzymatic reaction rate was correspondingly assessed by replacing the enzyme sample by buffer. The results are expressed as mg of GSH consumed/min/mg protein (Rotruck, J et al., 1973).

Reduced Glutathione [GSH]
Reagents:
1. 5% TCA: 5 g in 100 ml of distilled water.
2. Phosphate buffer (pH: 8) 0.2M
3. DTNB (0.6 mM): 12 mg in 50 ml PO4 buffer.

Protocol: Glutathione content was estimated according to the method (Moren et al 1979). 0.25 ml of serum was added to equal volume of ice cold 5% TCA. The precipitate was removed by centrifugation at 4000 rpm for 10 minutes. To 1 ml aliquot of supernatant, 0.25 ml of 0.2M phosphate buffer, pH 8.0 and 0.5 ml of DTNB (0.6 mM in 0.2M phosphate buffer, pH 8.0) was added and mixed well. The absorbance was read at 412 nm using spectrophotometer. The values were expressed in mg/g tissue.

Figure 9:
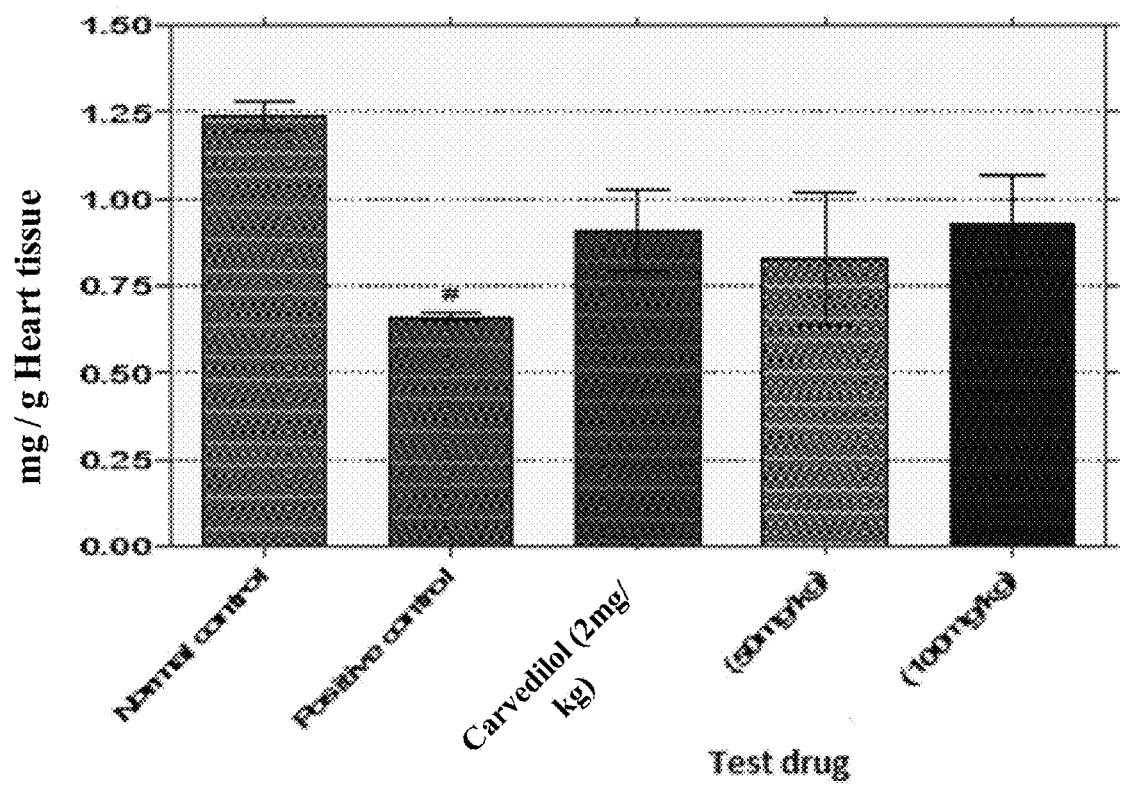
FIG. 9 depicts the effect of Test Drug on GSH activity.
Figure 10:
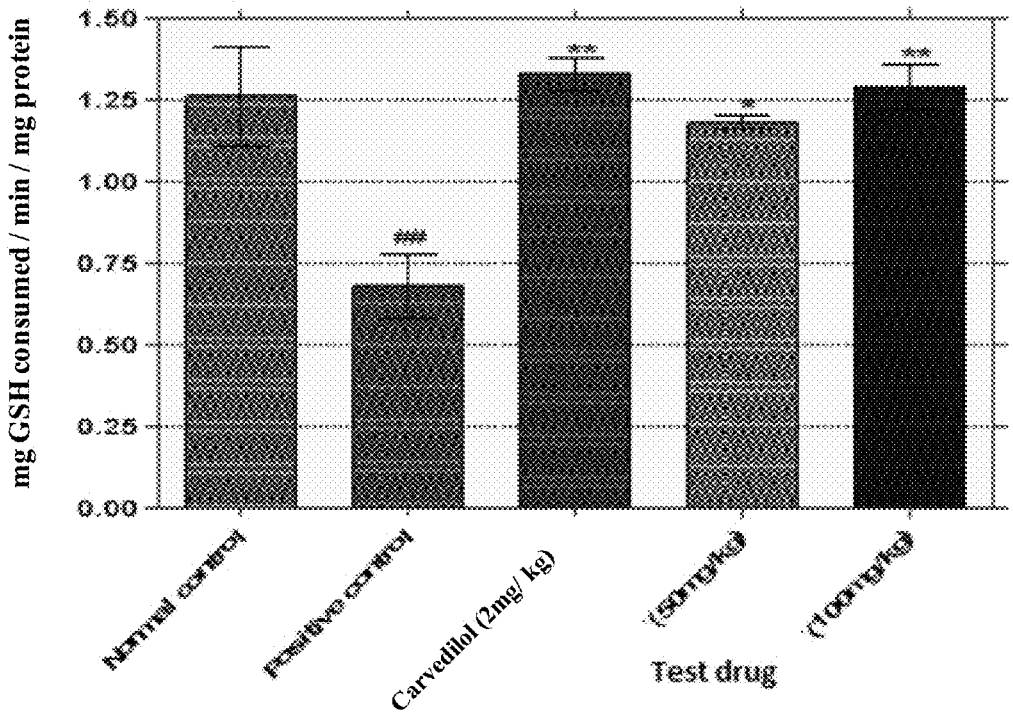
FIG. 10 depicts the effect of Test Drug on GPX activity.

GSH and Glutathione Peroxidase Activity:

FIG. 9 depicts GSH activity and FIG. 10 depicts GPX activity in the heart of normal and ISP induced rats. ISP induced in rats myocardial infarction showed significantly ($p<0.01$) decreased in anti-oxidants level of positive control group and significantly increased in GSH, GPX activities as compared to normal control group. Pretreatment with test drug dose dependently to ISP induced rats significantly increased the activities of these enzymes compared with positive control group. Glutathione is known to protect the myocardium against the free radicals mediated injury by the reduction of hydrogen peroxide, leads to decrease the reduced glutathione levels during the induction of cardiac necrosis (Kocak, H., et al., 1992). Depressed GSH levels with enhanced protective mechanism to oxidative stress in myocardial infarction. ISP administration was found to reduce the level of GSH in plasma and cardiac tissue (Ji et al., 1988). GPX and GST activities are significantly depressed in ISP induced rats. Endogenous enzymes inactivation of GPX in the heart leads to accumulation of oxidized glutathione (Ferrari R et al 1985). Inactivation of oxidized glutathione by enzymes containing sulphydryl group inhibit the protein synthesis (Ji et al 1988). In present study dose dependently increased in the activities of GSH, GPX on pretreatment with Test drug in ISP induced myocardial infarction group showed the antioxidant potential of Test drug against myocyte injury caused by free radicals.

Example 3(i)

Total Protein by Biuret Method

Reagents:
1. 0.2N sodium hydroxide
2. 0.5% copper sulphate (CuSO4.5H2O) in 1% potassium sodium tartrate.
3. Stock Biuret solution: Dissolve 4.5 g of sodium potassium tartarate in 40 ml of 0.2N NaOH. Then add 1.5 g of CuSO4 until completely dissolved. Finally add 500 mg of KI and make up the volume to 100 ml with 0.2N NaoH.
4. Working Biuret solution: From stock biuret solution 1:5 dilution.
5. Stock Protein solution: Weigh accurately 50 mg of bovine serum albumin (fraction V) and dissolve in distilled water and make up to 50 ml in standard flask.
6. Working standard: Dilute 10 ml of the stock solution to 50 ml with distilled water in a standard flask. One ml of this solution contains 200 µg protein.

Protocol: Estimation of protein was assayed by taking 0.2 ml of saline, 10% homogenate, followed by the addition of 1.25 ml of working biuret reagent. It was incubated at room temperature for 15 minutes. The color intensity was read at 540 nm.

Isoproterenol (ISP) injected rats (positive control) showed a significant decrease (P<0.001) in total protein levels as compared to control rats. Administration of test drug to ISP injected rats (Low dose) showed a significant (P<0.05) increase in the total protein level and highly significant increase in protein level (almost to normal level) is observed in both test drug group with high dose and standards (Carvedilol-2 mg/kg)

A decrease in the level of serum total proteins in Isoproterenol injected rats could be due to increased free radical production by Isoproterenol. Administration of test drug showed dose dependent improvement in serum protein levels as compared to ISP injected rats. This improvement is comparable to that of standard. Table 5 illustrates the effect of test drug on Total protein.

TABLE 5

Anti-Apoptosis (Gene expression)
Example 3(j): Reverse transcriptase (RT)

| Group | Treatment | Total protein (mg/dl) |
|---|---|---|
| I | Normal Control | 7.34 ± 0.37 |
| II | Positive Control | 3.58 ± 0.65 |
| III | Standard (Carvedilol- 2 mg/kg) | 7.24 ± 0.32 |
| IV | Low dose (50 mg/kg) | 6.89 ± 0.36 |
| V | High dose (100 mg/kg) | 7.31 ± 0.42 |

PCR was performed to determine the level of mRNA expression of Caspase, Bax, BCl2 and p53. Briefly, total RNA was extracted from left ventricle (Heart) using TRIzol Reagent (Sigma, USA). After homogenization, the tubes were incubated for 10 minutes and centrifuged at 1000 rpm for 5 min. 200 µl of chloroform was added to the supernatant, allowed to incubate for 5 min at room temperature and centrifuged at 12000 rcf for 20 min. Then 500 µl of isopropyl alcohol was added to the supernatant to precipitate the total RNA and centrifuged at 12000 rcf for 15 min following the incubation period of 10 min. The supernatant was decanted carefully; the pellet was washed three times with 75% ethanol, centrifuged at 12000 rcf for 15 min and the pellet was allowed to air dry. The pellet was resuspended in 20 µl of RNase free water and stored in −80° C. until use. The isolated RNA was allowed to undergo reverse transcription and polymerization reaction to get cDNA using PCR master cycler gradient. The formed cDNA was loaded in agarose gel, allowed to run the electrophoresis at 80V for 30 min and the gene expression was analyzed using the bands formed. 200 nanograms of RNA were used for reverse transcription polymerase chain reaction (RT-PCR) according to the manufacturer's instructions (Genet Bio, Korea). The following sequence was performed for each PCR reaction: 42.0 for 30 s, 94.0 for 5 min (1 cycle); 94° C. for 1 min, Caspase (56.0), Bax (58.8), Bcl2 (56.7) and p53 (57.9) for 1 min, and 72° C. for 1 min (with 35 cycles); and a final extension phase at 74° C. for 10 min.

The primer sequences (5'-3') used for the proteins Bax, Bcl2, Caspase 3 and P53 are as follows,

```
Bax-
(Forward primer)-
                                          SEQ ID NO: 1
GAGTGTCTCCGGCGAATTG (Reverse primer)-
                                          SEQ ID NO: 2
TGGTGAGCGAGGCGGTGAC Bcl2-
(Forward primer)-
                                          SEQ ID NO: 3
CGGGAGATCGTGATGAAGT (Reverse primer)-
                                          SEQ ID NO: 4
CCACCGAACTCAAAGAAGG Caspase 3-
(Forward primer)-
                                          SEQ ID NO: 5
CTGGACTGCGGTATTGAG (Reverse primer)-
                                          SEQ ID NO: 6
GGGTGCGGTAGAGTAAG P53-
(Forward primer)-
                                          SEQ ID NO: 7
GGATGCCCGTGCTGCCGAGGAG (Reverse primer)-
                                          SEQ ID NO: 8
AGTGAAGGGACTAGCATTGTC
```

Data Analysis

Statistical analysis was performed using GraphPad Prism, 4.03 (San Diego, US). Data were expressed as mean±SEM. Mean difference was analyzed by one way ANOVA with Tukey's multiple comparison as the post hoc test. Probability value less than 0.05 was fixed as the statistical significance criterion.

Figure 11:
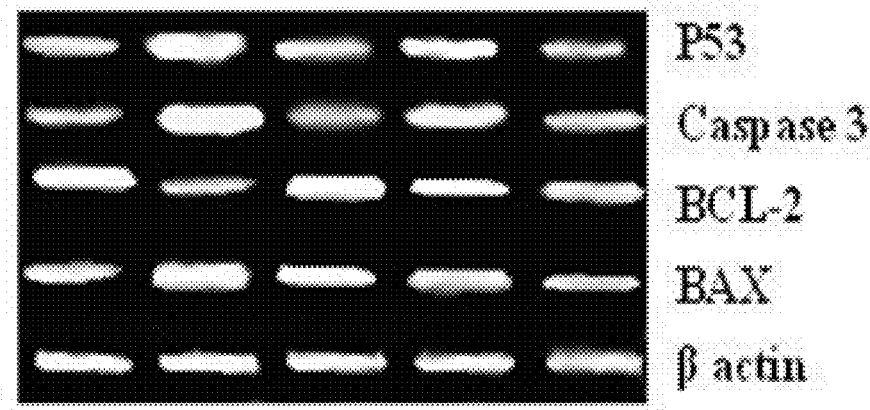
FIG. 11 depicts the effect of Test Drug on apoptotic markers.

Effect of Test Drug on Apoptotic Markers:

FIG. 11 illustrates the gene expression of apoptotic marker. Induction of myocardial infarction with ISP up-regulated the expression of apoptotic markers, Caspase 3, P53 and Bax and down regulated the expression of anti-apoptotic marker BCL-2. In the cascade of apoptosis, increased expression of Caspase 3 results in the phosphorylation of other caspases, on the other hand, P53 inhibits BCL-2 expression and conversely enhances Bax expression.

Bax in turn inhibits the Cytochrome C thereby augmenting the reactive oxygen species generation. BCL-2 and Bax proteins are known to modulate the cell survival signals of various apoptotic stimuli (Sutton, et al., 1997). Henceforth, we investigated the possible outcomes of Test drug treatment in ISP induced rats. Treatment with Test drug markedly up-regulated the expression of BCL-2, whereas down-regulated the expression of Caspase-3, P53 and Bax.

Clinical Observations:

No mortality was observed between the groups. The rats that were induced with isoproterenol showed increased heart rates and heart palpitation. Rigidity of the muscles was observed in the animals and there was decreased movement and activity in the animals. Exophthalmus, the protrusion of the eye balls, was very evident after the induction of isoproterenol. They exhibited increased respiration rate. Further, the symptoms of myocardial infarction were clearly visible in the ISP injected animals and the offset of these clinical signs prolonged in positive control.

Effect of Test Drug on Body Weight:

Table 6 depicts the body weight of animals for three weeks. No significant body weight changes were observed between the experimental groups on day 0, 7 and 14, whereas there was significant alteration in body weight on day 21.

TABLE 6

Body weight of animals for three weeks.

| Group | Treatment | Body weight (g) | | | |
|---|---|---|---|---|---|
| | | $0^{th}$ day | $7^{th}$ day | $14^{th}$ day | $21^{st}$ day |
| I | Normal Control | 201.29 ± 2.00 | 215.86 ± 2.50 | 223.43 ± 1.62 | 226.14 ± 3.19 |
| II | Positive Control | 206.86 ± 1.11 | 202.00 ± 1.19 | 202.71 ± 3.48 | 192.29 ± 1.44## |
| III | Standard (Carvedilol-2 mg/kg) | 211.00 ± 1.70 | 210.57 ± 3.22 | 218.43 ± 4.37 | 216.43 ± 1.58** |
| IV | Low dose (50 mg/kg) | 204.71 ± 6.04 | 207.57 ± 5.84 | 216.14 ± 2.97 | 203.29 ± 0.14** |
| V | High dose (100 mg/kg) | 202.00 ± 4.99 | 203.71 ± 4.37 | 207.14 ± 1.47 | 200.71 ± 0.39* |

Values were expressed in Mean ± SEM (n = 6);
, ##denotes P < 0.05 and 0.01 respectively (Comparison between Normal and Positive control);
*, **denotes P < 0.05 and 0.01 respectively (Comparison between Positive control and other treatment groups).

Effect of Test Drug on Organ Weight:

Table 7 depicts the organ weight of various groups. No significant difference in kidney and adrenals weight was observed between the treatment groups. The ISP induced MI rats showed increase in heart weight (24%) when compared to normal rats, whereas treatment with TEST DRUG altered the changes.

TABLE 7

Organ weight of various groups

| Group | Treatment | Organ weight (g) | | |
|---|---|---|---|---|
| | | Kidney | Adrenals | Heart |
| I | Normal Control | 0.85 ± 0.02 | 0.02 ± 0.01 | 0.41 ± 0.02 |
| II | Positive Control | 0.77 ± 0.06 | 0.02 ± 0.00 | 0.51 ± 0.02 (24%) |
| III | Standard (Carvedilol- 2 mg/kg) | 0.68 ± 0.10 | 0.02 ± 0.00 | 0.44 ± 0.07 (13.1%) |
| IV | Low dose (50 mg/kg) | 0.79 ± 0.02 | 0.02 ± 0.00 | 0.51 ± 0.02 (0.2%) |
| V | High dose (100 mg/kg) | 0.69 ± 0.09 | 0.02 ± 0.00 | 0.45 ± 0.06 (12.3%) |

Values were expressed in Mean ± SEM (n = 6);
Normal control was compared with positive and Positive control compared with other treatment groups.

Example 4

Clinical Study 150 hypertensive patients comprising 86 men and 74 women who were already on anti-hypertensives were advised to take Test drug along with their existing allopathic medicines. They were studied for a period of six weeks.

Dose: Two tablets (500 mg×02) were administered twice daily swallowed with water after food.

Results and Observation

Table 8 depicts Mean B.P before and after 3 and 6 weeks of Test drug administration (n=150).

TABLE 8

| | Mean systolic B.P | | | Mean diastolic B.P | | |
|---|---|---|---|---|---|---|
| Duration | Week 0 | Week 3 | Week 6 | Week 0 | Week 3 | Week 6 |
| MEAN | 167.12 | 131.2 | 125.12 | 104.76 | 84.16 | 81 |
| S.D. | 19.61 | 15.6 | 11.62 | 9.5 | 6.99 | 5.05 |
| S.E.M | ±0.71 | ±2.77 | ±1.64 | ±11.34 | ±0.98 | ±0.71 |

Figure 12:
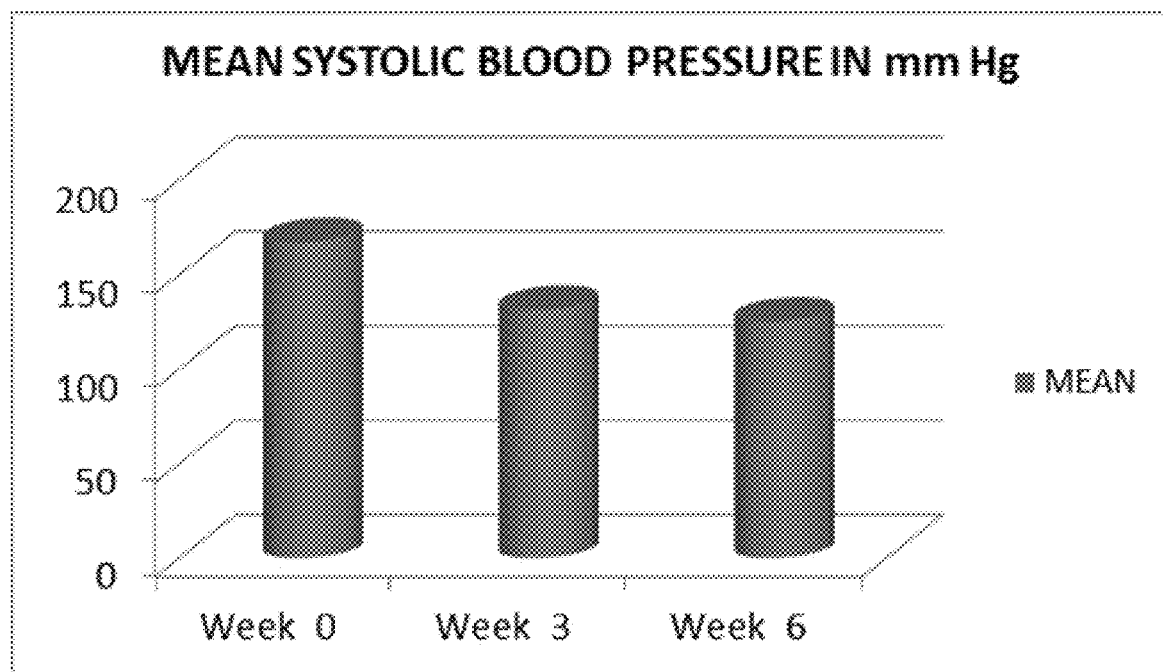
FIG. 12 depicts the effect of Test Drug Systolic Blood pressure.
Figure 13:
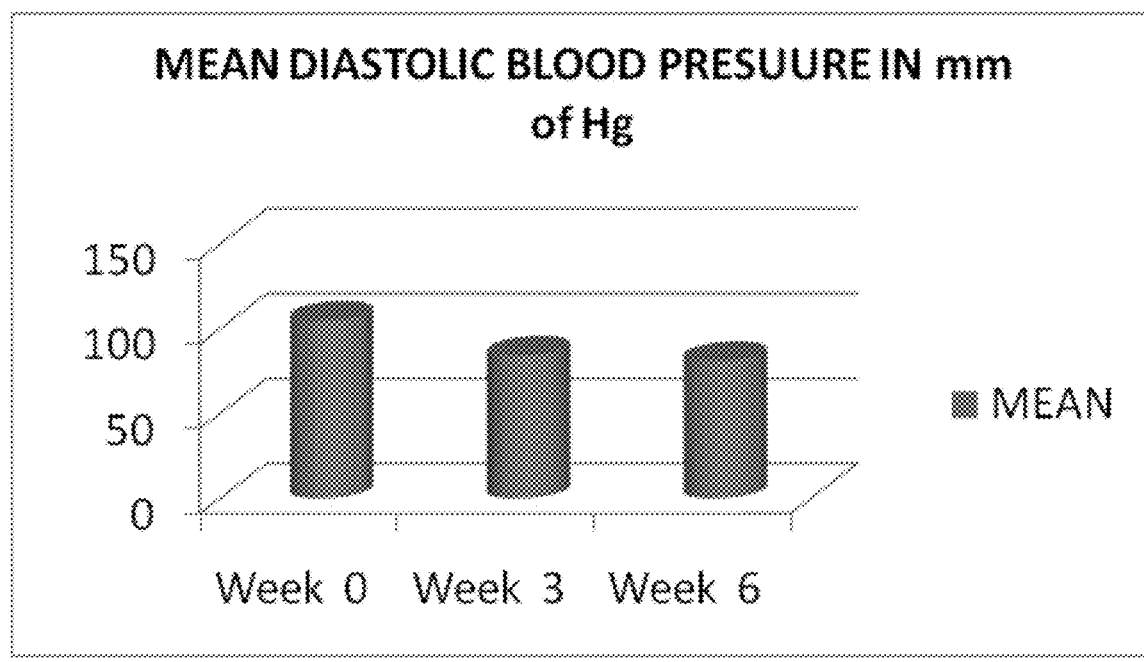
FIG. 13 depicts the effect of Test Drug Diastolic Blood pressure; according to embodiments as disclosed herein.

FIG. 12 illustrates the effect of Test drug on Systolic B.P. and FIG. 13 illustrates the effect of Test drug on Diastolic B.P.

After using the test drug, the resting pulse rates and blood pressure, both systolic and diastolic showed a significant reduction. In addition to helping in lowering of blood pressure and reduction of dosage of allopathic drugs there was also a feeling of general well-being. After the treatment with test drug for 6 months, there was an effective reduction in the dosages of the other anti-hypertensive drug in many cases.

Note: In a case of mitral valve prolapse with mild mitral regurgitation, when the test product was administered for 8 months follow up 2D Echocardiography confirmed that mitral valve prolapse is completely resolved and no mitral regurgitation was observed. Patient became asymptomatic, cardiac chambers and output were within normal limits.

The aforementioned studies proved that test product is free from toxicity. Preclinical study shows that test product exerts its Cardioprotective action through anti-apoptotic pathway in Isoproterenol induced experimental model of myocardial infarction. Clinical study supports antihypertensive, cardioprotective and valve correcting actions of the Test drug.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A formulation for treatment and management of Cardiovascular diseases, comprising:
   *Terminalia arjuna, Sida rhombifolia, Withania somnifera, Tinospora cordifolia, Punica granatum, Emblica officinalis* and *Commiphora mukul*, or extracts thereof, wherein *Terminalia arjuna* is present in an amount in the range of 8 to 12 wt %, *Sida rhombifolia* is present in an amount in the range of 2 to 6 wt %, *Withania somnifera* is present in an amount in the range of 2 to 6 wt %, *Tinospora cordifolia* is present in an amount in the range of 2 to 6 wt %, *Punica granatum* is present in an amount in the range of 2 to 6 wt %, *Emblica officinalis* is present in an amount in the range of 2 to 6 wt % and *Commiphora mukul* is present in an amount in the range of 2 to 6 wt %, of the total composition;
   shilajit in an amount in the range of 1 to 3 wt % of the total composition; and
   at least one bhasma selected from a group consisting of Muktasukti bhasma in an amount of ≤2 wt %, Loha bhasma in an amount of ≤2 wt %, Abhraka bhasma in an amount of ≤3 wt %, Swarnamakshika bhasma in an amount of ≤2 wt % and Pravala bhasma in an amount of ≤2 wt %, of the total composition.

2. The formulation as claimed in claim 1, wherein said formulation further comprises *Embelia ribes, Rubia cordifolia, Nardostachys jatamansi, Terminalia chebula, Terminalia bellerica, Piper longum, Piper nigrum, Zingiber officinalis, Boerhavia diffusa, Bamboo manna, Madhuca indica, Azadirachta indica, Picrorhiza kurroa, Holy basil, Stereospermum suaveolens, Premna mucronata, Gmelina arborea, Aegle marmelos, Oroxylum indicum, Desmodium gangeticum, Uraria picta, Solanum indicum, Solanum xanthocarpum,* and *Tribulus terrestris*; or extracts thereof.

3. The formulation as claimed in claim 2, wherein said formulation comprises *Embelia ribes* in an amount of ≤4 wt %, *Rubia cordifolia* in an amount of ≤4 wt %, *Nardostachys jatamansi* in an amount of ≤4 wt %, *Terminalia chebula* in an amount of ≤4 wt %, *Terminalia bellerica* in an amount of ≤4 wt %, *Piper longum* in an amount of ≤4 wt %, *Piper nigrum* in an amount of ≤4 wt %, *Zingiber officinalis* in an amount of ≤4 wt %, *Boerhavia diffusa* in an amount of ≤4 wt %, *Bamboo manna* in an amount of ≤4 wt %, *Madhuca indica* in an amount of ≤4 wt %, *Azadirachta indica* in an amount of ≤4 wt %, *Picrorhiza kurroa* in an amount of ≤4 wt %, *Holy basil* in an amount of ≤4 wt %, *Stereospermum suaveolens* in an amount of ≤4 wt %, *Premna mucronata* in an amount of ≤4 wt %, *Gmelina arborea* in an amount of ≤4 wt %, *Aegle marmelos* in an amount of ≤4 wt %, *Oroxylum indicum* in an amount of ≤4 wt %, *Desmodium gangeticum* in an amount of ≤4 wt %, *Uraria picta* in an amount of ≤4 wt %, *Solanum indicum* in an amount of ≤4 wt %, *Solanum xanthocarpum* in an amount of ≤4 wt %, and *Tribulus terrestris* in an amount of ≤4 wt %, of the total composition.

4. The formulation as claimed in claim 1, further comprising a suitable excipient.

5. The formulation as claimed in claim 4, wherein said excipient is gum acacia.

6. The formulation as claimed in claim 1, wherein said formulation is in the form of powder.

7. The formulation as claimed in claim 1, wherein said formulation is in the form of a tablet.

8. The formulation as claimed in claim 7, wherein said tablet is in the form of a 500 mg tablet.

9. A method for preparation of a medicament, comprising mixing an excipient and the formulation as claimed in claim 1.

10. A method of reducing the risks of Cardiovascular diseases, comprising administering to a patient in need thereof a therapeutically effective amount of the formulation claimed in claim 1.

11. A method for treatment and management of Cardiovascular diseases, comprising administering to a patient in need thereof a therapeutically effective amount of the formulation claimed in claim 1.

12. The method as claimed in claim 11, said method comprising administering two 500 mg tablets twice a day.

13. The method as claimed in claim 11, wherein said therapeutically effective amount is in the range of 500 to 1000 mg administered one to three times a day.

14. The method as claimed in claim 11, wherein said formulation is administered along with administration of at least one other medication prescribed for treatment of Cardiovascular diseases.

* * * * *